United States Patent [19]

Clayberger et al.

[11] Patent Number: 5,723,128
[45] Date of Patent: Mar. 3, 1998

[54] CYTOTOXIC T-CELL LYMPHOCYTE ("CTL") ACTIVITY REGULATION BY CLASS I MHC PEPTIDES

[75] Inventors: Carol Clayberger; Alan M. Krensky; Peter Parham, all of Stanford, Calif.

[73] Assignee: The Board of Trustees of the Leland Stanford Junior University, Stanford, Calif.

[21] Appl. No.: 222,851

[22] Filed: Apr. 5, 1994

Related U.S. Application Data

[63] Continuation-in-part of Ser. No. 844,716, Mar. 2, 1992, which is a continuation-in-part of Ser. No. 755,584, Sep. 3, 1991, abandoned, which is a continuation of Ser. No. 672,147, Mar. 19, 1991, abandoned, which is a continuation-in-part of Ser. No. 8,846, Jan. 30, 1987, abandoned.

[51] Int. Cl.$^6$ .............................. A61K 38/00; C07K 14/74
[52] U.S. Cl. ............................ 424/185.1; 424/184.1; 435/69.3; 530/300; 530/324; 530/395; 530/868; 514/2; 514/12
[58] Field of Search ..................... 424/184.1, 185.1; 514/2, 8, 12; 530/300, 324–350, 868, 403; 435/69.3

[56] References Cited

U.S. PATENT DOCUMENTS

| | | | |
|---|---|---|---|
| 4,634,590 | 1/1987 | Cohen et al. | 424/88 |
| 4,681,760 | 7/1987 | Fathman | 424/85.8 |
| 5,073,540 | 12/1991 | Olsson . | |
| 5,451,512 | 9/1995 | Apple et al. . | |

FOREIGN PATENT DOCUMENTS

| | | |
|---|---|---|
| WO 88/05784 | 8/1988 | WIPO . |
| WO 89/07448 | 8/1989 | WIPO . |
| WO 90/10016 | 9/1990 | WIPO . |
| WO 93/17699 | 9/1993 | WIPO . |

OTHER PUBLICATIONS

Auffray et al., *J. Human Immunology* (1986) 15:381–390.
Biddison et al., *J. Immunol.*, (1980) 124(2):548–552.
Clayberger et al., *J. Exp. Med.* (1985) 163:1709–1714.
Cowan et al., *J. Immunol.* (1985) 135:2835–2841.
Duran et al., *Transplantation*, (1986) 41(3):279–285.
Gaston et al., *J. Exp. Med.* (1983) 158:280–293.
Holmes et al., *EMBO Journal*, (1985) 4:2849–2854.
Koller et al., *J. Imunol.* (1985) 134:2727–2733.
Krangel et al., *Biochemistry* (1982) 21:6313–6321.
Krangel et al., *J. Immunol.* (1983) 130:1856–1862.
Krangel et al., *J. Exp. Med.* (1983) 157:324–336.
Nathenson et al., *Ann. Rev. Immunol.* (1986) 4:471–502.
Parham et al., *Chemical Abstracts* (1987) 106:516, abstract No. 154384 x.
Pease et al., *Proc. Natl. Acad. Sci.* (1983) 80:242–246.
Pierschbacher et al., *Nature* (1984) 309:30–33.
Salter et al., *J. Exp. Med.* (1987) 166:283–288.
Schulz et al., *Proc. Natl. Acad. Sci.* (1983) 80:2007–2011.
Spits et al., *Immunogenetics*, (1982) 16:503–512.
Taketani et al., *J. Immunol.* (1984) 133:816–821.
Towsend et al., (1986) Cell, (1986) 44:959–968.
Vega et al., *Proc. Natl. Acad. Sci.* (1985) 82:7394–7398.
Ways et al., *J. Biol. Chem.* (1985) 26:11924–11933.
Yamada et al., *J. Cell. Biol.* (1985) 28:99–104.
S. Nisco et al., *Journal of Immunology*, vol. 152, No. 8, pp. 3786–3792 (1994).
M.C. Cuturi et al., *Transplantation*, vol. 59, No. 9, pp. 661–669 (1995).
Clayberger et al., "Determinants Recognized by Human Cytotoxic T Cells on a Natural Hybrid Class 1 LA Molecule", *J. Exp. Med.*, 11:1709–1714 (1985).
Cowan et al. "Molecular Cloning and DNA Sequence Analysis of Genes Encoding Cytotxic T Lymphocyte–defined HLA–A3 Subtypes: The E1 Subtype", *J. of Immunology*, 135(4):2835–2840 (1985).
Gaston et al., "Epstein–Barr Virus–specific Cytotoxic T Lymphocytes as Probes of HLA Polymoorphism", *J. Exp. Med.*, 158:280–293 (1983).
Holmes and Parham, "Exon Shuffling in vivo can Generate Novel HLA Class I Molecules", *Eur. Mol. Biol. Organ J.*, 4(11):2849–2854 (1985).
Nisco et al., "Induction of Allograft Tolerance in Rats by an HLA Class–I–Derived Peptide and Cyclosporine A$^{1}$", *J. of Immunology*, 152:3786–3792 (1994).
Pierschbacher and Ruoslahti, "Cell Attachment Activity of Fibronectin can be Duplicated by Small Synthetic Fragments of the Molecule", *Nature*, 309:30–33 (1984).
Salter et al., "In vitro Mutagenesis at a Single Residue Introduces B and T Cell Epitopes into a Class I HLA Molecule", *J. Exp. Med.*, 166:283–288 (1987).
Townsend et al., "The Epitopes of Influenza Nucleoprotein Recognized by Cytotoxic T Lymphocytes can be Defined with Short Synthetic Peptides", *Cell*, 44:959–968 (1986).
Vega et al., "Structural Analysis of an HLA–B27 Functional Variant: Identification of Residues that Contribute to the Specificity of Recognition by Cytolytic T Lymphocytes", *Proc. Natl. Acad. Sci. USA*, 82:7394–7398 (1985).
Chen, et al., "Cytotoxic T Cell Recognition of an Endogenous Class I HLA Peptide Presented by a Class II HLA Molecule," *J. Exp. Med.* (1990) 172:779–788.
Rojo, et al., "HLA–B27 Antigenicity: Antibodies Against the Chemically Synthesized 63–84 Peptide from HLA–B27.1 Display Alloantigenic Specificity and Discriminate Among HLA–B27 Subtypes," *J. Immunol.* (1986) 137:904–910.
Raybourne, et al., "Monoclonal Antibodies Against an HLA–B27–Derived Peptide React with an Epitope Present on Bacterial Proteins," *J. Immunol.* (1990) 145:2539–2544.
Heath, et al., "Mapping of Epitopes Recognized by Allorective Cytotoxic T Lymphocytes Usig Inhibition by MHC Peptides," *J. Immunol.* (1989) 143:1441–1446.

*Primary Examiner*—Thomas M. Cunningham
*Attorney, Agent, or Firm*—Morrison & Foerster LLP

[57] ABSTRACT

Fragments from the polymorphic domains of Class I HLA antigen domains are used to modulate T-cell activity. The peptides are from the α1- or α2 domains, particularly of the HLA-A, and B antigens. The peptides may be conjugated to other compounds to be used in diagnosis and therapy. The peptides may block lysis, CTL proliferation or have other regulating effects.

16 Claims, 9 Drawing Sheets

FIG. 4

SEQUENCE LISTING ( 1 ) GENERAL INFORMATION:

( i i i ) NUMBER OF SEQUENCES: 43

( 2 ) INFORMATION FOR SEQ ID NO:1:

( i ) SEQUENCE CHARACTERISTICS:
( A ) LENGTH: 274 amino acids
( B ) TYPE: amino acid
( C ) STRANDEDNESS: single
( D ) TOPOLOGY: linear ( x i ) SEQUENCE DESCRIPTION: SEQ ID NO:1:

```
Gly Ser His Ser Met Arg Tyr Phe Tyr Thr Ser Val Ser Arg Pro Gly
1               5                   10                  15

Arg Gly Glu Pro Arg Phe Ile Ala Val Gly Tyr Val Asp Asp Thr Gln
            20                  25                  30

Phe Val Arg Phe Asp Ser Asp Ala Ala Ser Pro Arg Met Glu Pro Arg
        35                  40                  45

Ala Pro Trp Ile Glu Gln Glu Gly Pro Glu Tyr Trp Asp Arg Glu Thr
    50                  55                  60

Gln Ile Val Lys Ala Gln Ser Gln Thr Asp Arg Glu Asp Leu Arg Thr
65                  70                  75                  80

Leu Arg Gly Tyr Tyr Asn Gln Ser Glu Ala Gly Ser His Thr Ile Gln
                85                  90                  95

Arg Met Tyr Gly Cys Asp Val Gly Pro Asp Gly Arg Leu Leu Arg Gly
            100                 105                 110

Tyr His Gln Tyr Ala Tyr Asp Gly Lys Asp Tyr Ile Ala Leu Asn Glu
        115                 120                 125

Asp Leu Arg Ser Trp Thr Ala Ala Asp Thr Ala Ala Gln Ile Thr Gln
    130                 135                 140

Arg Lys Trp Glu Ala Ala Arg Val Ala Glu Gln Leu Arg Ala Tyr Leu
145                 150                 155                 160

Glu Gly Thr Cys Val Glu Trp Leu Arg Arg Tyr Leu Glu Asn Gly Lys
                165                 170                 175

Glu Thr Leu Gln Arg Ala Asp Pro Pro Lys Thr His Val Thr His His
            180                 185                 190

Pro Ile Ser Asp His Glu Ala Thr Leu Arg Cys Trp Ala Leu Gly Phe
```

-continued

```
                195                          200                          205
Tyr   Pro   Ala   Glu   Ile   Thr   Leu   Thr   Trp   Gln   Arg   Asp   Gly   Glu   Asp   Gln
      210                            215                     220

Thr   Gln   Asp   Thr   Glu   Leu   Val   Glu   Thr   Arg   Pro   Ala   Gly   Asp   Gly   Thr
225                           230                            235                           240

Phe   Gln   Lys   Trp   Ala   Ala   Val   Val   Val   Pro   Ser   Gly   Glu   Glu   Gln   Arg
                  245                            250                           255

Tyr   Thr   Cys   His   Val   Gln   His   Glu   Gly   Leu   Pro   Lys   Pro   Leu   Thr   Leu
                  260                            265                           270

Arg   Trp
```

( 2 ) INFORMATION FOR SEQ ID NO:2:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i x ) FEATURE:
        ( A ) NAME/KEY: Region
        ( B ) LOCATION: 1..4
        ( D ) OTHER INFORMATION: /note= "Amino acids 80-84 of
            B17(Bw58) sequence shown in Fig. 4"

( x i ) SEQUENCE DESCRIPTION: SEQ ID NO:2:

```
Ile   Ala   Leu   Arg
1
```

( 2 ) INFORMATION FOR SEQ ID NO:3:

( i ) SEQUENCE CHARACTERISTICS:
        ( A ) LENGTH: 66 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 1
        ( D ) OTHER INFORMATION: /product="OTHER"
            / label= aa55
            / note= "Glutamic acid (E) or Lysine (K), particularly E"

( i x ) FEATURE:
        ( A ) NAME/KEY: Modified-site
        ( B ) LOCATION: 8
        ( D ) OTHER INFORMATION: /product="OTHER"
            / label= aa62
            / note= "Glycine (G), glutamine (Q), glutamic acid (E) or
            arginine (R), particularly R or G"

( i x ) FEATURE:
        ( A ) NAME/KEY: Modified-site
        ( B ) LOCATION: 9
        ( D ) OTHER INFORMATION: /product="OTHER"
            / label= aa63
            / note= "An acidic amino acid or amide thereof,
            particularly glutamic acid (E)"

( i x ) FEATURE:
        ( A ) NAME/KEY: Modified-site
        ( B ) LOCATION: 11
        ( D ) OTHER INFORMATION: /product="OTHER"
            / label= aa65
            / note= "Glutamine (Q), Arginine (R) or Glycine (G),
            particularly Q or R"

( i x ) FEATURE:
        ( A ) NAME/KEY: Modified-site
        ( B ) LOCATION: 12
        ( D ) OTHER INFORMATION: /product="OTHER"

/ label= aa66
/ note= "Isoleucine (I), asparagine (N) or lysine (K), particularly I or K"

( i x ) FEATURE:
    ( A ) NAME/KEY: Modified-site
    ( B ) LOCATION: 13
    ( D ) OTHER INFORMATION: /product="OTHER"
        / label= aa67
        / note= "An aliphatic neutral or Y amino acid, particularly cysteine(C), serine(S), valine(V) or tyrosine(Y)"

( i x ) FEATURE:
    ( A ) NAME/KEY: Modified-site
    ( B ) LOCATION: 15
    ( D ) OTHER INFORMATION: /product="OTHER"
        / label= aa69
        / note= "An aliphatic neutral or basic amino acid, particularly alanine(A), arginine(R) or threonine(T)"

( i x ) FEATURE:
    ( A ) NAME/KEY: Modified-site
    ( B ) LOCATION: 16
    ( D ) OTHER INFORMATION: /product="OTHER"
        / label= aa70
        / note= "Glutamine(Q), histidine(H), serine(S), asparagine(N) or lysine(K)"

( i x ) FEATURE:
    ( A ) NAME/KEY: Modified-site
    ( B ) LOCATION: 17
    ( D ) OTHER INFORMATION: /product="OTHER"
        / label= aa71
        / note= "An aliphatic neutral amino acid, particularly alanine (A), leucine (L), serine (S) or threonine (T)"

( i x ) FEATURE:
    ( A ) NAME/KEY: Modified-site
    ( B ) LOCATION: 20
    ( D ) OTHER INFORMATION: /product="OTHER"
        / label= aa74
        / note= "Aspartic acid (D), tyrosine (Y) or histidine (H)"

( i x ) FEATURE:
    ( A ) NAME/KEY: Modified-site
    ( B ) LOCATION: 22
    ( D ) OTHER INFORMATION: /product="OTHER"
        / label= aa76
        / note= "Glutamic acid (E) or valine (V)"

( i x ) FEATURE:
    ( A ) NAME/KEY: Modified-site
    ( B ) LOCATION: 23
    ( D ) OTHER INFORMATION: /product="OTHER"
        / label= aa77
        / note= "Aspartic acid (D), serine (S) or asparagine (N)"

( i x ) FEATURE:
    ( A ) NAME/KEY: Modified-site
    ( B ) LOCATION: 25
    ( D ) OTHER INFORMATION: /product="OTHER"
        / label= aa79
        / note= "Arginine (R) or glycine (G)"

( i x ) FEATURE:
    ( A ) NAME/KEY: Modified-site
    ( B ) LOCATION: 26
    ( D ) OTHER INFORMATION: /product="OTHER"
        / label= aa80
        / note= "Threonine (T), isoleucine (I) or asparagine (N)"

( i x ) FEATURE:
    ( A ) NAME/KEY: Modified-site
    ( B ) LOCATION: 27
    ( D ) OTHER INFORMATION: /product="OTHER"
        / label= aa81
        / note= "An aliphatic non-polar amino acid, particularly alanine (A) or leucine (L)"

( i x ) FEATURE:
         ( A ) NAME/KEY: Modified-site
         ( B ) LOCATION: 28
         ( D ) OTHER INFORMATION: /product="OTHER"
                 / label= aa82
                 / note= "Arginine (R) or leucine (L)"

( i x ) FEATURE:
         ( A ) NAME/KEY: Modified-site
         ( B ) LOCATION: 29
         ( D ) OTHER INFORMATION: /product="OTHER"
                 / label= aa83
                 / note= "Glycine (G) or arginine (R)"

( i x ) FEATURE:
         ( A ) NAME/KEY: Modified-site
         ( B ) LOCATION: 40
         ( D ) OTHER INFORMATION: /product="OTHER"
                 / label= aa94
                 / note= "Threonine (T) or isoleucine (I)"

( i x ) FEATURE:
         ( A ) NAME/KEY: Modified-site
         ( B ) LOCATION: 41
         ( D ) OTHER INFORMATION: /product="OTHER"
                 / label= aa95
                 / note= "A non-polar aliphatic amino acid of from five to
                 six carbon atoms"

( i x ) FEATURE:
         ( A ) NAME/KEY: Modified-site
         ( B ) LOCATION: 43
         ( D ) OTHER INFORMATION: /product="OTHER"
                 / label= aa97
                 / note= "An aliphatic amino acid or tryptophan (W)"

( i x ) FEATURE:
         ( A ) NAME/KEY: Modified-site
         ( B ) LOCATION: 45
         ( D ) OTHER INFORMATION: /product="OTHER"
                 / label= aa99
                 / note= "An aromatic amino acid"

( i x ) FEATURE:
         ( A ) NAME/KEY: Modified-site
         ( B ) LOCATION: 49
         ( D ) OTHER INFORMATION: /product="OTHER"
                 / label= aa103
                 / note= "A non-polar aliphatic amino acid of from five to
                 six carbon atoms"

( i x ) FEATURE:
         ( A ) NAME/KEY: Modified-site
         ( B ) LOCATION: 51
         ( D ) OTHER INFORMATION: /product="OTHER"
                 / label= aa105
                 / note= "Proline (P) or serine (S)"

( i x ) FEATURE:
         ( A ) NAME/KEY: Modified-site
         ( B ) LOCATION: 53
         ( D ) OTHER INFORMATION: /product="OTHER"
                 / label= aa107
                 / note= "Glycine (G) or tryptophan (W)"

( i x ) FEATURE:
         ( A ) NAME/KEY: Modified-site
         ( B ) LOCATION: 55
         ( D ) OTHER INFORMATION: /product="OTHER"
                 / label= aa109
                 / note= "Leucine (L) or phenylalanine (F)"

( i x ) FEATURE:
         ( A ) NAME/KEY: Modified-site
         ( B ) LOCATION: 59
         ( D ) OTHER INFORMATION: /product="OTHER"
                 / label= aa113
                 / note= "Tyrosine (Y) or histidine (H)"

( i x ) FEATURE:

(A) NAME/KEY: Modified-site
(B) LOCATION: 60
(D) OTHER INFORMATION: /product="OTHER"
/ label= aa114
/ note= "Histidine (H), glutamine (Q), aspartic acid (D), asparagine (N) or arginine (R)"

(ix) FEATURE:
(A) NAME/KEY: Modified-site
(B) LOCATION: 62
(D) OTHER INFORMATION: /product="OTHER"
/ label= aa116
/ note= "Tyrosine (Y), aspartic acid (D), serine (S), phenylalanine (F) or histidine (H)"

(xi) SEQUENCE DESCRIPTION: SEQ ID NO:3:

| Xaa | Gly | Pro | Glu | Tyr | Trp | Asp | Xaa | Xaa | Thr | Xaa | Xaa | Xaa | Lys | Xaa | Xaa |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Xaa | Gln | Thr | Xaa | Arg | Xaa | Xaa | Leu | Xaa | Xaa | Xaa | Xaa | Xaa | Tyr | Tyr | Asn |
|     |     |     | 20  |     |     |     |     | 25  |     |     |     |     | 30  |     |     |
| Gln | Ser | Glu | Ala | Gly | Ser | His | Xaa | Xaa | Gln | Xaa | Met | Xaa | Gly | Cys | Asp |
|     |     | 35  |     |     |     |     | 40  |     |     |     |     | 45  |     |     |     |
| Xaa | Gly | Xaa | Asp | Xaa | Arg | Xaa | Leu | Arg | Gly | Xaa | Xaa | Gln | Xaa | Ala | Tyr |
|     | 50  |     |     |     | 55  |     |     |     |     |     | 60  |     |     |     |     |
| Asp | Gly |     |     |     |     |     |     |     |     |     |     |     |     |     |     |
| 65  |     |     |     |     |     |     |     |     |     |     |     |     |     |     |     |

(2) INFORMATION FOR SEQ ID NO:4:

(i) SEQUENCE CHARACTERISTICS:
(A) LENGTH: 37 amino acids
(B) TYPE: amino acid
(C) STRANDEDNESS: single
(D) TOPOLOGY: linear (ix) FEATURE:
(A) NAME/KEY: Modified-site
(B) LOCATION: 9
(D) OTHER INFORMATION: /note= "glycine (G) or arginine (R)"

(ix) FEATURE:
(A) NAME/KEY: Modified-site
(B) LOCATION: 10
(D) OTHER INFORMATION: /note= "glutamic acid (E) or asparagine (N)"

(ix) FEATURE:
(A) NAME/KEY: Modified-site
(B) LOCATION: 12
(D) OTHER INFORMATION: /note= "arginine (R) or glutamine (Q)"

(ix) FEATURE:
(A) NAME/KEY: Modified-site
(B) LOCATION: 13
(D) OTHER INFORMATION: /note= "lysine (K) or asparagine (N)"

(ix) FEATURE:
(A) NAME/KEY: Modified-site
(B) LOCATION: 17
(D) OTHER INFORMATION: /note= "histidine (H) or glutamine (Q)"

(ix) FEATURE:
(A) NAME/KEY: Modified-site
(B) LOCATION: 21
(D) OTHER INFORMATION: /note= "histidine (H) or aspartic acid (D)"

(ix) FEATURE:
(A) NAME/KEY: Modified-site
(B) LOCATION: 23
(D) OTHER INFORMATION: /note= "valine (V) or glutamic acid (E)"

(ix) FEATURE:

(A) NAME/KEY: Modified-site
(B) LOCATION: 24
(D) OTHER INFORMATION: /note= "aspartic acid (D), serine (S) or asparagine (N)"

(ix) FEATURE:
(A) NAME/KEY: Modified-site
(B) LOCATION: 26
(D) OTHER INFORMATION: /note= "glycine (G) or arginine (R)"

(ix) FEATURE:
(A) NAME/KEY: Modified-site
(B) LOCATION: 27
(D) OTHER INFORMATION: /note= "threonine (T) or isoleucine (I)"

(ix) FEATURE:
(A) NAME/KEY: Modified-site
(B) LOCATION: 28
(D) OTHER INFORMATION: /note= "leucine (L) or alanine (A)"

(ix) FEATURE:
(A) NAME/KEY: Modified-site
(B) LOCATION: 29
(D) OTHER INFORMATION: /note= "arginine (R) or leucine (L)"

(ix) FEATURE:
(A) NAME/KEY: Modified-site
(B) LOCATION: 30
(D) OTHER INFORMATION: /note= "glycine (G) or arginine (R)"

(xi) SEQUENCE DESCRIPTION: SEQ ID NO:4:

```
Gln Glu Gly Pro Glu Tyr Trp Asp Xaa Xaa Thr Xaa Xaa Val Lys Ala
1               5                   10                  15
Xaa Ser Gln Thr Xaa Arg Xaa Xaa Leu Xaa Xaa Xaa Xaa Xaa Tyr Tyr
                20                  25                  30
Asn Gln Ser Glu Ala
            35
```

(2) INFORMATION FOR SEQ ID NO:5:

(i) SEQUENCE CHARACTERISTICS:
(A) LENGTH: 19 amino acids
(B) TYPE: amino acid
(C) STRANDEDNESS: single
(D) TOPOLOGY: linear (xi) SEQUENCE DESCRIPTION: SEQ ID NO:5:

```
Thr Leu Gln Arg Met Tyr Gly Cys Asp Val Gly Ser Asp Trp Arg Phe
1               5                   10                  15
Leu Arg Gly
```

(2) INFORMATION FOR SEQ ID NO:6:

(i) SEQUENCE CHARACTERISTICS:
(A) LENGTH: 16 amino acids
(B) TYPE: amino acid
(C) STRANDEDNESS: single
(D) TOPOLOGY: linear (xi) SEQUENCE DESCRIPTION: SEQ ID NO:6:

```
Met Tyr Gly Cys Asp Val Gly Ser Asp Trp Arg Phe Leu Arg Gly Tyr
1               5                   10                  15
```

(2) INFORMATION FOR SEQ ID NO:7:

(i) SEQUENCE CHARACTERISTICS:
(A) LENGTH: 16 amino acids
(B) TYPE: amino acid
(C) STRANDEDNESS: single
(D) TOPOLOGY: linear ( x i ) SEQUENCE DESCRIPTION: SEQ ID NO:7:

Met Tyr Gly Cys Asp Val Gly Ser Asp Gly Arg Phe Leu Arg Gly Tyr
1               5                   10                  15

( 2 ) INFORMATION FOR SEQ ID NO:8:

( i ) SEQUENCE CHARACTERISTICS:
      ( A ) LENGTH: 14 amino acids
      ( B ) TYPE: amino acid
      ( C ) STRANDEDNESS: single
      ( D ) TOPOLOGY: linear ( x i ) SEQUENCE DESCRIPTION: SEQ ID NO:8:

Gly Pro Glu Tyr Trp Asp Gly Glu Thr Arg Lys Val Lys Ala
1               5                   10

( 2 ) INFORMATION FOR SEQ ID NO:9:

( i ) SEQUENCE CHARACTERISTICS:
      ( A ) LENGTH: 26 amino acids
      ( B ) TYPE: amino acid
      ( C ) STRANDEDNESS: single
      ( D ) TOPOLOGY: linear ( i x ) FEATURE:
      ( A ) NAME/KEY: Modified-site
      ( B ) LOCATION: 21
      ( D ) OTHER INFORMATION: /note= "Isoleucine or Threonine"

( i x ) FEATURE:
      ( A ) NAME/KEY: Modified-site
      ( B ) LOCATION: 22
      ( D ) OTHER INFORMATION: /note= "Alanine or Leucine"

( x i ) SEQUENCE DESCRIPTION: SEQ ID NO:9:

Trp Asp Arg Glu Thr Gln Ile Cys Lys Ala Lys Ala Gln Thr Asp Arg
1               5                   10                  15

Asn Asx Leu Arg Xaa Xaa Leu Arg Tyr Tyr
                20              25

( 2 ) INFORMATION FOR SEQ ID NO:10:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( x i ) SEQUENCE DESCRIPTION: SEQ ID NO:10:

Trp Asp Arg Glu Thr Gln Lys Tyr Lys Arg Gln Ala Gln Thr Asp Arg
1               5                   10                  15

Val Ser Leu Arg Asn Leu Arg Gly Tyr
                20              25

( 2 ) INFORMATION FOR SEQ ID NO:11:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( x i ) SEQUENCE DESCRIPTION: SEQ ID NO:11:

Trp Asp Arg Glu Thr Gln Ile Ser Lys Thr Asn Thr Gln Thr Tyr Arg
1               5                   10                  15

Glu Ser Leu Arg Asn Leu Arg Gly Tyr
                20              25

( 2 ) INFORMATION FOR SEQ ID NO:12:

( i ) SEQUENCE CHARACTERISTICS:
      ( A ) LENGTH: 25 amino acids
      ( B ) TYPE: amino acid
      ( C ) STRANDEDNESS: single
      ( D ) TOPOLOGY: linear ( x i ) SEQUENCE DESCRIPTION: SEQ ID NO:12:

Trp Asp Gly Glu Thr Arg Lys Val Lys Ala His Ser Gln Thr His Arg
   1               5                   10                  15

Val Asp Leu Gly Thr Leu Arg Gly Tyr
                   20                  25

( 2 ) INFORMATION FOR SEQ ID NO:13:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( x i ) SEQUENCE DESCRIPTION: SEQ ID NO:13:

Arg Glu Asn Leu Arg Ile Ala Leu Arg Tyr
   1               5                   10

( 2 ) INFORMATION FOR SEQ ID NO:14:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( x i ) SEQUENCE DESCRIPTION: SEQ ID NO:14:

Arg Glu Asp Leu Arg Thr Leu Leu Arg Tyr
   1               5                   10

( 2 ) INFORMATION FOR SEQ ID NO:15:

( i ) SEQUENCE CHARACTERISTICS:
      ( A ) LENGTH: 10 amino acids
      ( B ) TYPE: amino acid
      ( C ) STRANDEDNESS: single
      ( D ) TOPOLOGY: linear ( x i ) SEQUENCE DESCRIPTION: SEQ ID NO:15:

Trp Asp Arg Glu Thr Gln Ile Cys Lys Ala
   1               5                   10

( 2 ) INFORMATION FOR SEQ ID NO:16:

( i ) SEQUENCE CHARACTERISTICS:
      ( A ) LENGTH: 4 amino acids
      ( B ) TYPE: amino acid
      ( C ) STRANDEDNESS: single
      ( D ) TOPOLOGY: linear ( x i ) SEQUENCE DESCRIPTION: SEQ ID NO:16:

Asp Gly Glu Thr
   1

( 2 ) INFORMATION FOR SEQ ID NO:17:

( i ) SEQUENCE CHARACTERISTICS:
      ( A ) LENGTH: 4 amino acids
      ( B ) TYPE: amino acid ( C ) STRANDEDNESS: single
( D ) TOPOLOGY: linear ( x i ) SEQUENCE DESCRIPTION: SEQ ID NO:17:

Gly Glu Thr Arg
1

( 2 ) INFORMATION FOR SEQ ID NO:18:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:18:

Asp Arg Ala Thr
1

( 2 ) INFORMATION FOR SEQ ID NO:19:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:19:

Tyr Trp Asp Gly
1

( 2 ) INFORMATION FOR SEQ ID NO:20:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:20:

Arg Glu Asx Leu
1

( 2 ) INFORMATION FOR SEQ ID NO:21:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( i x ) FEATURE:
( A ) NAME/KEY: Modified-site
( B ) LOCATION: 1
( D ) OTHER INFORMATION: /note= "Alanine or Leucine"

( x i ) SEQUENCE DESCRIPTION: SEQ ID NO:21:

Xaa Leu Arg Tyr
1

( 2 ) INFORMATION FOR SEQ ID NO:22:

( i ) SEQUENCE CHARACTERISTICS:
( A ) LENGTH: 4 amino acids
( B ) TYPE: amino acid
( C ) STRANDEDNESS: single
( D ) TOPOLOGY: linear ( x i ) SEQUENCE DESCRIPTION: SEQ ID NO:22:

Ser Thr Trp Arg
1

( 2 ) INFORMATION FOR SEQ ID NO:23:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( x i ) SEQUENCE DESCRIPTION: SEQ ID NO:23:

Ser Asp Gly Arg
1

( 2 ) INFORMATION FOR SEQ ID NO:24:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i x ) FEATURE:
        ( A ) NAME/KEY: Modified-site
        ( B ) LOCATION: 5
        ( D ) OTHER INFORMATION: /note= "Valine, Isoleucine, or
            Leucine"

( i x ) FEATURE:
        ( A ) NAME/KEY: Modified-site
        ( B ) LOCATION: 17
        ( D ) OTHER INFORMATION: /note= "Tryptophan or Glycine"

( x i ) SEQUENCE DESCRIPTION: SEQ ID NO:24:

Gly Ser His Thr Xaa Gln Arg Met Tyr Gly Cys Asp Val Gly Ser Asp
1               5                   10                  15

Xaa Arg Phe Leu Arg Gly Tyr His Gln Tyr Ala Tyr Asp Gly
        20                  25                  30

( 2 ) INFORMATION FOR SEQ ID NO:25:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( x i ) SEQUENCE DESCRIPTION: SEQ ID NO:25:

Arg Glu Xaa Leu Arg Xaa Xaa Xaa Xaa Tyr
1               5                   10

( 2 ) INFORMATION FOR SEQ ID NO:26:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( x i ) SEQUENCE DESCRIPTION: SEQ ID NO:26:

Trp Asp Arg Glu Thr Gln Ile Cys Lys Ala Lys Ala Gln Thr Asp Arg
1               5                   10                  15

Glu Asn Leu Arg Ile Ala Leu Arg Tyr
        20                  25

( 2 ) INFORMATION FOR SEQ ID NO:27:

( i ) SEQUENCE CHARACTERISTICS:

(A) LENGTH: 25 amino acids
(B) TYPE: amino acid
(C) STRANDEDNESS: single
(D) TOPOLOGY: linear (xi) SEQUENCE DESCRIPTION: SEQ ID NO:27:

Trp Asp Arg Glu Thr Gln Ile Cys Lys Ala Lys Ala Gln Thr Asp Arg
1               5                   10                  15

Glu Asp Leu Arg Thr Leu Leu Arg Tyr
            20              25

(2) INFORMATION FOR SEQ ID NO:28:

(i) SEQUENCE CHARACTERISTICS:
(A) LENGTH: 25 amino acids
(B) TYPE: amino acid
(C) STRANDEDNESS: single
(D) TOPOLOGY: linear (xi) SEQUENCE DESCRIPTION: SEQ ID NO:28:

Arg Lys Trp Glu Ala Ala Arg Val Ala Glu Gln Leu Arg Ala Tyr Leu
1               5                   10                  15

Glu Gly Glu Cys Val Glu Trp Leu Arg
            20              25

(2) INFORMATION FOR SEQ ID NO:29:

(i) SEQUENCE CHARACTERISTICS:
(A) LENGTH: 25 amino acids
(B) TYPE: amino acid
(C) STRANDEDNESS: single
(D) TOPOLOGY: linear (xi) SEQUENCE DESCRIPTION: SEQ ID NO:29:

Trp Asp Arg Asn Thr Gln Ile Cys Lys Thr Asn Thr Gln Thr Tyr Arg
1               5                   10                  15

Glu Asn Leu Arg Ile Ala Leu Arg Tyr
            20              25

(2) INFORMATION FOR SEQ ID NO:30:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO:30:

Arg Glu Asp Leu Arg Ile Ala Leu Arg Tyr
1               5                   10

(2) INFORMATION FOR SEQ ID NO:31:

(i) SEQUENCE CHARACTERISTICS:
(A) LENGTH: 10 amino acids
(B) TYPE: amino acid
(C) STRANDEDNESS: single
(D) TOPOLOGY: linear (xi) SEQUENCE DESCRIPTION: SEQ ID NO:31:

Arg Glu Asn Leu Arg Thr Ala Leu Arg Tyr
1               5                   10

(2) INFORMATION FOR SEQ ID NO:32:

(i) SEQUENCE CHARACTERISTICS:
(A) LENGTH: 10 amino acids

```
            ( B ) TYPE: amino acid
            ( C ) STRANDEDNESS: single
            ( D ) TOPOLOGY: linear ( x i ) SEQUENCE DESCRIPTION: SEQ ID NO:32:

Arg  Glu  Asn  Leu  Arg  Ile  Leu  Leu  Arg  Tyr
1                  5                        10
```

( 2 ) INFORMATION FOR SEQ ID NO:33:

```
    ( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( x i ) SEQUENCE DESCRIPTION: SEQ ID NO:33:

Tyr  Arg  Leu  Ala  Ile  Arg  Leu  Asn  Glu  Arg  Glu  Asn  Leu  Arg  Ile
1                  5                        10                       15

Ala  Leu  Arg  Tyr
                20
```

( 2 ) INFORMATION FOR SEQ ID NO:34:

```
    ( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( x i ) SEQUENCE DESCRIPTION: SEQ ID NO:34:

Tyr  Arg  Leu  Ala  Thr  Arg  Leu  Asn  Glu  Arg  Glu  Asn  Leu  Arg  Ile
1                  5                        10                       15

Ala  Leu  Arg  Tyr
                20
```

( 2 ) INFORMATION FOR SEQ ID NO:35:

```
    ( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( x i ) SEQUENCE DESCRIPTION: SEQ ID NO:35:

Tyr  Arg  Leu  Ala  Ile  Arg  Leu  Asn  Glu  Arg  Glu  Asn  Leu  Arg  Thr
1                  5                        10                       15

Ala  Leu  Arg  Tyr
                20
```

( 2 ) INFORMATION FOR SEQ ID NO:36:

```
    ( i ) SEQUENCE CHARACTERISTICS:
            ( A ) LENGTH: 20 amino acids
            ( B ) TYPE: amino acid
            ( C ) STRANDEDNESS: single
            ( D ) TOPOLOGY: linear ( x i ) SEQUENCE DESCRIPTION: SEQ ID NO:36:

Tyr  Arg  Leu  Ala  Thr  Arg  Leu  Asn  Glu  Arg  Glu  Asn  Leu  Arg  Thr
1                  5                        10                       15

Ala  Leu  Arg  Tyr
                20
```

( 2 ) INFORMATION FOR SEQ ID NO:37:

( i ) SEQUENCE CHARACTERISTICS:
   ( A ) LENGTH: 20 amino acids
   ( B ) TYPE: amino acid
   ( C ) STRANDEDNESS: single
   ( D ) TOPOLOGY: linear ( x i ) SEQUENCE DESCRIPTION: SEQ ID NO:37:

Tyr Arg Leu Ala Ile Arg Leu Asn Glu Arg Tyr Arg Leu Ala Ile Arg
1               5                   10                  15

Leu Asn Glu Arg
         20

( 2 ) INFORMATION FOR SEQ ID NO:38:

( i ) SEQUENCE CHARACTERISTICS:
     ( A ) LENGTH: 15 amino acids
     ( B ) TYPE: amino acid
     ( C ) STRANDEDNESS: single
     ( D ) TOPOLOGY: linear ( x i ) SEQUENCE DESCRIPTION: SEQ ID NO:38:

Lys Ala Gln Thr Asp Arg Glu Asn Leu Arg Ile Ala Leu Arg Tyr
1               5                   10                  15

( 2 ) INFORMATION FOR SEQ ID NO:39:

( i ) SEQUENCE CHARACTERISTICS:
     ( A ) LENGTH: 10 amino acids
     ( B ) TYPE: amino acid
     ( C ) STRANDEDNESS: single
     ( D ) TOPOLOGY: linear ( x i ) SEQUENCE DESCRIPTION: SEQ ID NO:39:

Arg Glu Ser Leu Arg Asn Leu Arg Gly Tyr
1               5                   10

( 2 ) INFORMATION FOR SEQ ID NO:40:

( i ) SEQUENCE CHARACTERISTICS:
     ( A ) LENGTH: 20 amino acids
     ( B ) TYPE: amino acid
     ( C ) STRANDEDNESS: single
     ( D ) TOPOLOGY: linear ( x i ) SEQUENCE DESCRIPTION: SEQ ID NO:40:

Tyr Gly Arg Leu Asn Arg Leu Ser Glu Arg Arg Glu Ser Leu Arg Asn
1               5                   10                  15

Leu Arg Gly Tyr
         20

( 2 ) INFORMATION FOR SEQ ID NO:41:

( i ) SEQUENCE CHARACTERISTICS:
     ( A ) LENGTH: 10 amino acids
     ( B ) TYPE: amino acid
     ( C ) STRANDEDNESS: single
     ( D ) TOPOLOGY: linear ( x i ) SEQUENCE DESCRIPTION: SEQ ID NO:41:

Arg Val Asp Leu Arg Thr Leu Arg Gly Tyr
1               5                   10

( 2 ) INFORMATION FOR SEQ ID NO:42:

( i ) SEQUENCE CHARACTERISTICS:
     ( A ) LENGTH: 10 amino acids
     ( B ) TYPE: amino acid
     ( C ) STRANDEDNESS: single -continued (D) TOPOLOGY: linear (ix) FEATURE:
    (A) NAME/KEY: Modified-site
    (B) LOCATION: group(3, 7..9)
    (D) OTHER INFORMATION: /note= "Amino acids selected from the group consisting of C, S, T, M, G, L, I, P, V, N, Q, E, K and R"

(xi) SEQUENCE DESCRIPTION: SEQ ID NO:42:

```
Arg Glu Xaa Leu Arg Ile Xaa Xaa Xaa Tyr
 1               5                   10
```

(2) INFORMATION FOR SEQ ID NO:43:

(i) SEQUENCE CHARACTERISTICS:
    (A) LENGTH: 10 amino acids
    (B) TYPE: amino acid
    (C) STRANDEDNESS: single
    (D) TOPOLOGY: linear (ix) FEATURE:
    (A) NAME/KEY: Modified-site
    (B) LOCATION: group(3, 7)
    (D) OTHER INFORMATION: /note= "Amino acids selected from the group consisting of C, S, T, M, G, L, I, P, V, N, Q, E, K and R"

(xi) SEQUENCE DESCRIPTION: SEQ ID NO:43:

```
Arg Glu Xaa Leu Arg Ile Xaa Leu Arg Tyr
 1               5                   10
```

CYTOTOXIC T-CELL LYMPHOCYTE ("CTL") ACTIVITY REGULATION BY CLASS I MHC PEPTIDES

CROSS REFERENCE TO RELATED APPLICATIONS

This application is a continuation-in-part of application, Ser. No. 07/844,716, filed Mar. 2, 1992 (now pending), which is a continuation-in-part of application, Ser. No. 07/755,584, filed Sep. 3, 1991 (abandoned), which is a continuation of application, Ser. No. 07/672,147, filed Mar. 19, 1991 (abandoned), which is a continuation-in-part of application, Ser. No. 07/008,846, filed Jan. 30, 1987 (abandoned).

INTRODUCTION

1. Technical Field

The field of this invention is the regulation of cytotoxic T-lymphocytes using peptide fragments from Class I MHC peptides.

2. Background

Cytotoxic T-cells, particularly cytotoxic T-lymphocytes ("CTL"), are restricted in their activity by recognizing a specific histocompatibility complex ("MHC") antigen on the surface of the target cell, as well as a peptide bound in a cleft of the MHC antigen. The foreign antigen may be as a result of transplantation from an allogeneic host, viral infection, mutation, neoplasia, or the like. The involvement of the MHC protein appears to be essential to the attack by CTLs against the cell which includes the foreign antigen. By monitoring the presence of foreign antigens, the CTLs are able to destroy cells, which if otherwise allowed to proliferate, might result in the proliferation of pathogens or neoplastic cells.

In monitoring the presence of foreign antigens, the CTLs also recognize transplants of organs, tissues and cells, which come from allogeneic or xenogeneic hosts. In order to protect the transplant from the CTLs, various immunosuppressive procedures are employed. These procedures involve employing, for the most part, immunosuppressive drugs which inhibit the entire immune system and put the patient at risk to opportunistic infection. Furthermore, the treatment frequently must be maintained at some level during the life of the patient, subjecting the patient to the deleterious effects of the drug in addition to the susceptibility to disease. In addition, it is frequently found that the procedures are not sufficiently protective, so as to maintain the transplant.

In view of the very great interest in providing for enhanced opportunities for successful transplantation, as well as other situations where there is an interest in modulating CTL activity, there are substantial opportunities for developing new techniques which improve on the present therapeutic treatments involving modulating CTL activity.

Relevant Literature

Clayberger, et al., *J. Exp. Med.* (1985) 11:1709–1714 describe HLA-A2 antigen in comparisons with HLA-Aw68 and Aw69. Townsend, et al., *Cell*, (1986) 44:959–968 suggests that CTL recognize segmental epitopes of denatured or degraded proteins in a similar way as helper T-cells. Holmes and Parham, *EMBO J.*, (1985) 4:2849–2854 describe the relationship of HLA-A2, Aw68 and Aw69. CTL target specificity has been taught to be extremely sensitive to changes in structure of human Class I molecules (Durna and Pease, *Transplantation*, (1986)41:279–285; Biddison, et al., *J. Immunol.*, (1980) 124:548–552; Spits, et al., *Immunogenetics*, (1982) 16:503–512; Gaston, et al., *J. Exp. Med.* (1983) 158:280–293).

Mutants which affect recognition by CTL have been studied in mice (Nathenson, et al., *Ann. Rev. Immunol.* (1986) 4:471–502; Schulz, et al., *Proc. natl. Acad. Sci. USA* (1983) 80:2007–2011) and humans, (Krangel, *Biochemistry* (1982) 21:6313–6321; Krangel, et al., *J. Immunol.* (1983) 130:1856–1862; Cowan, et al., *J. Immunol.* (1985) 135:2835–2841; Taketani, et al., ibid (1984) 133:816–821; and Vega, et al., *Proc. Natl. Acad. Sci. USA* (1985) 82:7394–7398).

These reports have focused considerable attention on the region between residues 147 and 157, although other regions can also produce functional differences (Ezquerra, et al., *J. Immunol.* (1985) 134:2727–2733). Clusters of variability have been reported at the carboxy-terminal end of the first extracellular domain and at the amino-terminal end of the second extracellular domain (Ways, et al., *J. Biol. Chem.* (1985) 26:11924–11933). Sequences between residues 105–108 of all Class I molecules are related to that of the fibronectin binding tetrapeptide (Auffray and Novotny, *J. Human Immunology* (1986) 15:381–390), which tetrapeptide in either orientation is found to have cell attachment properties (Pierschbacher and Ruoslahti, *Nature* (1984) 309:30–33; Yamada and Kennedy, *J. Cell. Biol.* (1985) 28:99–104). Substitution at position 107 affecting a single monoclonal antibody defined epitope of HLA-A2 has been reported by Salter, et al., *J. Exp. Med.* (1987) 166:283–288.

SUMMARY OF THE INVENTION

Methods and compositions are provided based on the sequence of Class I antigen $\alpha 1$- and $\alpha 2$- domains, particularly $\alpha 1$- domains, and more particularly $\alpha 1$- domains comprising amino acids 75-84. The fragments include at least a portion of the amino acids between positions 55 and 120 of the Class I antigens and are used for modulating cytotoxic T-lymphocyte differentiation and/or lysis of target cells. Different peptides may elicit different effects in relation to CTLs or subsets of CTLs.

Of particular interest is the use of peptides or peptide oligomers to improve the outcome of organ transplants by administering the peptide in conjunction with a predetermined regimen of a subtherapeutic amount of an immunosuppressant for a limited period of time.

The subject invention also includes purified proteins having molecular weight of 70 and 74 which serve as binding targets of subject peptides.

BRIEF DESCRIPTION OF THE DRAWINGS

FIG. 4 (SEQ ID NO:1 and SEQ ID NO:2) shows the consensus sequence of peptides which constitute the $\alpha 1$, $\alpha 2$ and $\alpha 3$ regions of a Class I HLA molecule, as well as changes in these sequences in different specific HLA molecules.

DESCRIPTION OF SPECIFIC EMBODIMENTS

Figure 1:
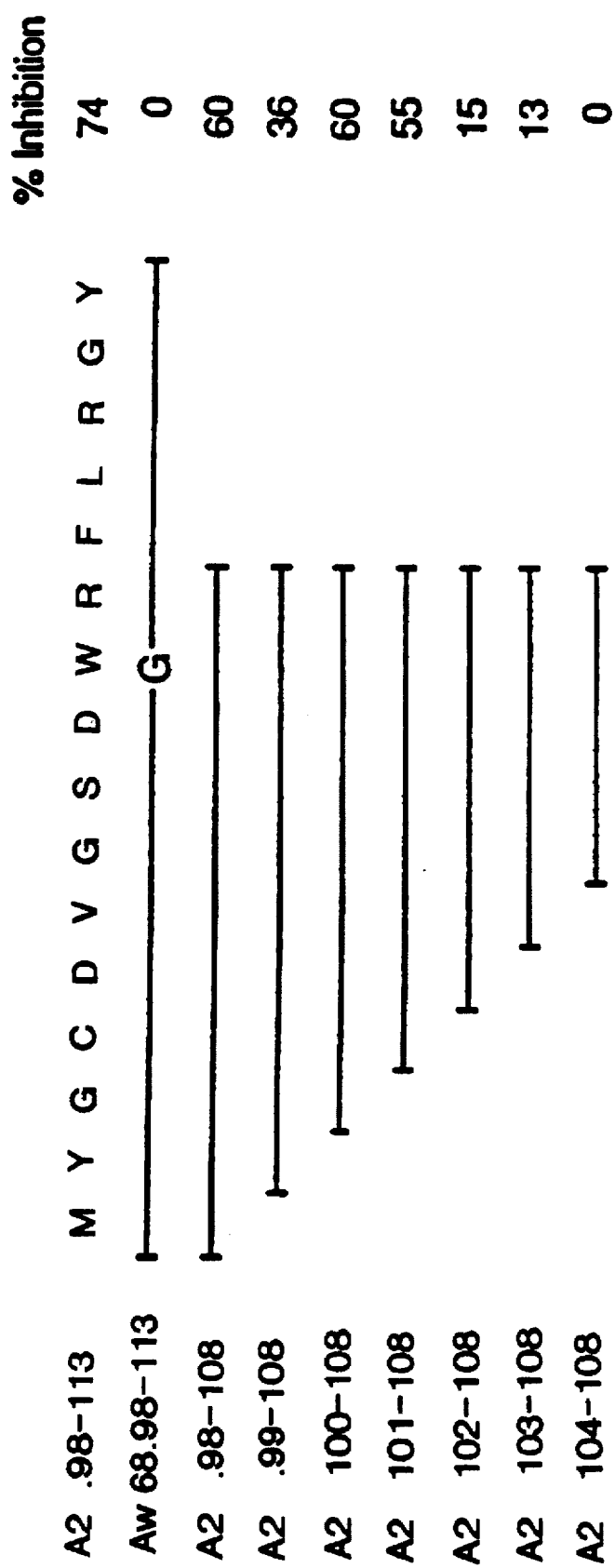
FIG. 1 shows the minimum size of peptide sequence required for inhibition of cytolysis by HLA-A2 specific CTL.

In accordance with the subject invention, CTL activity in a patient is modulated, particularly inhibited, by administering to the patient a sequence of the polymorphic region of one or more Class I major histocompatibility complex antigens, from the host or foreign to the host. Also the peptides provide for inhibiting binding of CTLs to targets of the CTLs, where the effect may be due to inhibition of the differentiation of CTLs and/or inhibition of lysis of target cells by CTLs.

The polymorphic region comprises the α1- and α2-domains, where the α1- domain is of particular interest, more particularly, the α1- domain comprising amino acids 75-84. The Class I antigens in the human are designated A, B, and C, where other animals have analogous classes, of which the A and B antigens are of particular interest. More particularly, specific peptides are of interest, which are found to be relatively non-specific to the Class I MHC of the target cells in providing for CTL activity modulation. Therefore, one may distinguish between peptide sequences which will be relatively specific as to the Class I MHC to which they bind and peptides which are relatively non-specific, binding to CTLs having a broad range of Class I MHC antigens. The subject peptides may be used as monomers, as oligomers, or bound to a wide variety of molecules to provide for specific characteristics, such as enhanced physiological stability, multifunctional properties, ease of administration.

In addition to modulation of CTL activity, the subject peptides may be used in a variety of other ways. The subject peptides may be used to identify particular CTLs which bind to the peptide; they may be used for removing CTLs or subsets of CTLs from a T-cell composition or portion thereof; they may be used in assays for detecting agents having comparable activity, where the agent may be used to compete with the subject peptides for the peptide target in a competitive assay; they may be used in rational drug design for defining a particular structure of interest; and the like. For the most part, the subject compositions will comprise pure compositions or formulated compositions of a peptide of at least eight amino acids, more usually at least ten amino acids, usually at least 12 amino acids, having a sequence coming within the extended sequence and up to the entire extended sequence (SEQ ID NO:3):

$aa^{55}$ G P E Y W D $aa^{62}$ $aa^{63}$ T $aa^{65}$ $aa^{66}$ $aa^{67}$ K $aa^{69}$ $aa^{70}$ $aa^{71}$ Q T $aa^{74}$ R $aa^{76}$ $aa^{77}$ L $aa^{79}$ $aa^{80}$ $aa^{81}$ $aa^{82}$ $aa^{83}$ Y Y N Q S E A G S H $aa^{94}$ $aa^{95}$ Q $aa^{97}$ M $aa^{99}$ G C D $aa^{103}$ G $aa^{105}$ D $aa^{107}$ R $aa^{109}$ L R G $aa^{113}$ $aa^{114}$ Q $aa^{116}$ A Y D G wherein:

$aa^{55}$ is E or K, particularly E;

$aa^{62}$ is G, Q, E or R, particularly R or G;

$aa^{63}$ is an acidic amino acid or amide thereof, particularly E;

$aa^{65}$ is Q, R or G, particularly Q or R;

$aa^{66}$ is I, N or K, particularly I or K;

$aa^{67}$ is an aliphatic neutral or Y amino acid, particularly C, S, V or Y;

$aa^{69}$ is an aliphatic neutral or basic amino acid, particularly A, R or T;

$aa^{70}$ is Q, H, S, N or K;

$aa^{71}$ is an aliphatic neutral amino acid, particularly A, L, S or T;

$aa^{74}$ is D, Y or H;

$aa^{76}$ is E or V;

$aa^{77}$ is D, S or N;

$aa^{79}$ is R or G;

$aa^{80}$ is T, I or N;

$aa^{81}$ is an aliphatic non-polar amino acid, particularly A or L;

$aa^{82}$ is R or L;

$aa^{83}$ is G or R;

$aa^{94}$ is T or I;

$aa^{95}$ is a non-polar aliphatic amino acid of from five to six carbon atoms;

$aa^{97}$ is an aliphatic amino acid or W;

$aa^{99}$ is an aromatic amino acid;

$aa^{103}$ is a non-polar aliphatic amino acid of from five to six carbon atoms;

$aa^{105}$ is P or S;

$aa^{107}$ is G or W;

$aa^{109}$ is L or F;

$aa^{113}$ is Y or H;

$aa^{114}$ is H, Q, D, N or R;

$aa^{116}$ is Y, D, S, F or H, or mutants of the subject compositions, normally having not more than two substitutions, usually not more than one substitution, where the substitution is at a site which does not affect the modulation of the CTL activity; where the subject peptides modulate CTL activity.

A subset of peptides of particular interest come within the following extended sequence (Amino acids 37 to 66 of SEQ ID NO:3):

G S H $aa^{94}$ $aa^{95}$ Q $aa^{97}$ M $aa^{99}$ G C D $aa^{103}$ G $aa^{105}$ D $aa^{107}$ R $aa^{109}$ L R

G $aa^{113}$ $aa^{114}$ Q $aa^{116}$ A Y D G wherein:

$aa^{94}$ is T or I;

$aa^{95}$ is a non-polar aliphatic amino acid of from five to six carbon atoms;

$aa^{97}$ is an aliphatic amino acid or W;

$aa^{99}$ is an aromatic amino acid;

$aa^{103}$ is a non-polar aliphatic amino acid of from five to six carbon atoms;

$aa^{105}$ is P or S;

$aa^{107}$ is G or W;

$aa^{109}$ is L or F;

$aa^{113}$ is Y or H;

$aa^{114}$ is H, Q, D, N or R;

$aa^{116}$ is Y, D, S, F or H.

Another subset of sequences coming within the above-extended sequence of particular interest are sequences coming within the extended sequence (Amino acids 1 to 36 SEQ ID NO:3):

$aa^{55}$ G P E Y W D $aa^{62}$ $aa^{63}$ T $aa^{65}$ $aa^{66}$ $aa^{67}$ K $aa^{69}$ $aa^{70}$ $aa^{71}$ Q T $aa^{74}$ R $aa^{76}$ $aa^{77}$ L $aa^{79}$ $aa^{80}$ $aa^{81}$ $aa^{82}$ $aa^{83}$ Y Y N Q S E A wherein:

$aa^{55}$ is E or K, particularly E;

$aa^{62}$ is G, Q, E or R, particularly R or G;

$aa^{63}$ is an acidic amino acid or amide thereof, including E and N, particularly E;

$aa^{65}$ is Q, R or G, particularly Q or R;

$aa^{66}$ is I, N or K, particularly N or K;

$aa^{67}$ is an aliphatic neutral amino acid including V, M, S, C and Y, particularly V;

$aa^{69}$ is an aliphatic neutral amino acid including A, T and P, particularly A;

$aa^{70}$ is Q, H, S, N or K, particularly Q or H;

$aa^{71}$ is an aliphatic neutral amino acid including S, A and T, particularly S;

$aa^{74}$ is D, Y or H, particularly D or H;

$aa^{76}$ is E or V;

$aa^{77}$ is D, S or N, particularly D;

$aa^{79}$ is R or G, particularly G;

$aa^{80}$ is T, I or N, particularly T or I;

$aa^{81}$ is an aliphatic non-polar amino acid including L or A, particularly L;

$aa^{82}$ is R or L, particularly R;

$aa^{83}$ is G or R, particularly G.

Another series of peptides of at least eight amino acids, usually of at least about ten amino acids, of particular interest come within the extended sequence (SEQ ID NO:4):

Q E G P E Y W D (G or R) (E or N) T (R or Q) (K or N) V K A (H or Q) S Q T (H or D) R (V or E) (D, S or N) L (G or R) (T or I) (L or A) (R or L) (G or R) Y Y N Q S E A.

Other extended sequences from which eight amino acid fragments are of interest include (SEQ ID NO:5 through SEQ ID NO:12):

T L Q R M Y G C D V G S D W R F L R G,

M Y G C D V G S D W R F L R G Y,

M Y G C D V G S D G R F L R G Y,

G P E Y W D G E T R K V K A,

W D R E T Q I C K A K A Q T D R N (N or D) L R (I or T) (A or L) L R Y Y,

W D R E T Q K Y K R Q A Q T D R V S L R N L R G Y,

W D R E T Q I S K T N T Q T Y R E S L R N L R G Y, and

W D G E T R K V K A H S Q T H R V D L G T L R G Y.

Of particular interest are the shorter sequences (SEQ ID NO:15 through SEQ ID NO:15):

R E N L R I A L R Y;
R E D L R T L L R Y; and
W D R E T Q I C K A.

Among the sequences of interest are the sequences in the α1-domain, namely the amino acid sequence from positions 55–85, more particularly 55–80 or 70–85, desirably including within the sequence a tetrapeptide DGET, GETR, DRAT, YWDG, RE(N or D)L or (A or L)LRY (SEQ ID NO:16 through SEQ ID NO:26). Of particular interest for the α2-domain is the amino acid sequence from positions 90–112, more particularly 94–116, desirably including within the sequence a tetrapeptide STWR (SEQ ID NO:22) or SDGR (SEQ ID NO:23).

The peptides of interest which will serve as the receptor binding peptide will have at least eight amino acids, usually at least ten amino acids, more usually at least 12 amino acids, frequently having 15 or more amino acids, and usually not more than about 30 amino acids, more usually not more than about 24 amino acids, desirably having about 12 to 21 amino acids. The amino acid sequence will usually not differ from a naturally occurring sequence by more than 2 amino acid substitutions, or mutations, e.g. deletions or insertions, more usually by not more than about 1 amino acid. The sequence employed will usually be from the polymorphic regions of the C-terminal half of the α1 domain or the N-terminal half of the α2 domain of the MHC antigen of the host of the MHC restricted T-cells, particularly an HLA-A or -B group antigen, where the peptides are active only with cells having the same MHC antigen or substantially homologous antigen, or from a different host or mutated sequence, where the sequence acts with a range of T cells from hosts having different Class I MHC antigens. These sequences which act across a number of hosts having different Class I MHC antigens, particularly A and B, more particularly B, may be considered pan-sequences.

Of particular interest is a sequence or sequence fragment of at least eight amino acids of the sequence (SEQ ID NO:24):

| |
|---|
| G S H T (V, I or L) Q R M Y G C D V G S D (W or G) R F L R G Y H Q Y A Y D G. |

Where there are two or more amino acids indicated at the same site, any of the indicated amino acids may be present.

The region of particular interest will be the region from amino acid positions 110 to 116.

The subject peptides may be modified in a wide variety of ways. The peptides may be joined by covalent bonds at any convenient site along the peptide to a variety of other compounds for different purposes. Thus, the peptides may be joined to immunogens for administration to a host for immunization for production of antibodies, or may be joined to a non-adjacent MHC sequence of the particular MHC antigen by means of synthesis, expression of a synthetic gene, or the like; joined to a lipid or polyalkyleneoxy group; joined to a sugar; or joined to a nucleic acid. Of particular interest is joining the subject peptides to another peptide by synthesis or expression of a synthetic gene where the other peptide provides for extended stability of the subject peptides when administered to a host. Various peptides may be used, such as the immunoglobulin constant region, e.g. IgG Fc. Alternatively, the subject peptides may be joined to a toxin, such as diphtheria toxin, ricin, abrin, etc., particularly where the binding chain has been removed or inactivated, so as to prevent binding of the binding chain to cells.

Of particular interest are peptides from HLA-B7 or -27, more particularly -2702, where one or more amino acids may be substituted, while retaining CTL modulating activity. B7 and B2702 differ at sites 77, 80, 81, 82 and 83, having identity at sites 75, 76, 78, 79, and 84. Furthermore, it is found that the amino acid at sites 77 and 81 may be substituted without loss of CTL modulating activity. Thus, a consensus sequence is $REX^1LRX^2X^3X^4X^5Y$, where $X^1$ may be any amino acid, polar or non-polar, preferably polar, either charged or non-charged; $X^2$ is preferably an amino acid of at least five carbon atoms, which may be polar or non-polar, particularly asparagine and isoleucine; $X^3$ may be any amino acid, particularly non-polar aliphatic of from two to six carbon atoms, more particularly three to five carbon atoms; $X^4$ may be any amino acid, particularly aliphatic, either charged or non-charged, preferably at least about five carbon atoms, such as arginine and leucine; $X^5$ may be any amino acid, preferably aliphatic, charged or non-charged, polar or non-polar, particularly glycine and arginine. Preferably, $X^{1-5}$ will be S, N, L, R, G or N, I, A, L, R, respectively, where one of the amino acids in one group may be substituted at the same site for the amino acid in the other group.

Besides being joined to each other, either through a bond or through a polypeptide bridge, of from about 1–30 amino acids, more usually of from about 1–20 amino acids, where the subject peptides may be joined to a polyfunctional backbone, so as to have a plurality of the subject peptides bonded to the backbone, where the subject peptide may be joined by other than amino acids. Thus, various linking groups may be employed where the subject peptides may be modified to provide for a convenient functionality for linking. By synthesizing the subject peptides, various functionalities may be introduced such as thiol, carboxy, amino, hydroxy, phosphate, or the like, where these groups may then be used for linking to aliphatic, aromatic, alicyclic, or heterocyclic groups, usually having from about 1–30, more usually from about 1–20 carbon atoms. Thus, polyvinyl alcohols, acrylic acids, polysaccharides, or the like may be employed to provide for convenient backbones upon which to bond the subject oligopeptides.

Usually, in the oligomers of the subject peptides, there will be at least two and not more than about 20, usually not more than about ten oligomers.

In considering conservative substitutions, the classes of amino acids are designated as follows:

| | |
|---|---|
| aliphatic | |
| non-polar | G, A, P, L, I, V |
| polar | |
| neutral | C, S, T, M, N, Q |
| acidic | D, E |
| basic | K, R |
| aromatic | F, H, W, Y |

For the most part, amino acids indicated on a single line will be conservative substitutions, although usually a conservative substitution will differ by fewer than three carbon atoms from the substituting amino acid. Also, in many cases, the charge or polarity will not be as important as the size, so that L, I, V, N, Q, E, K and R may be substituted one for the other, that is one aliphatic group for another aliphatic group.

The peptides may be prepared in a variety of ways. Conveniently, they can be synthesized by conventional techniques employing automatic synthesizers, such as the Beckman, Applied Biosystem Inc., or other useful peptide synthesizer apparatus, or may be synthesized manually. Alternatively, DNA sequences can be prepared which encode the particular peptide and may be cloned and expressed to provide the desired peptide. In this instance a methionine may be the first amino acid.

The peptides may also be isolated from natural sources and purified by known techniques, including, for example, chromatography on ion exchange materials, separation by size, immunoaffinity chromatography and electrophoresis.

As used herein, the term "a substantially pure preparation of peptide compound" means a preparation of the peptide which is usually greater than about 70% free of materials with which the polypeptide is naturally associated, and preferably greater than about 80% free of these materials; these materials, however, excludes materials with which the peptide may be mixed in the preparation of pharmaceutical compositions. The sequences may be modified in a variety of ways depending upon their ultimate purpose. Different N- or C-terminal groups may be introduced which allow for linking of the peptide to solid substrates or other molecules. In a synthetic procedure, any molecule may be introduced at the N- or C-terminus which would allow for subsequent reaction, depending upon the purpose for which the peptide is prepared.

For diagnostic purposes, a wide variety of labels may be linked to the terminus, which may provide, directly or indirectly, a detectable signal. For example, fluorescers may be introduced at the terminus or other molecules which provide a linkage to labels such as fluorescers, enzymes, particles, or the like. For example, linkage may be introduced at the terminus, e.g., biotin, which will bind to an avidin conjugate with enzymes or fluorescers. Alternatively, various reactive sites may be introduced at the terminus for linking to particles, solid substrates, macromolecules, or the like. For example, an internal amino moiety of a growing chain bound to a solid substrate with the intermediate side groups protected, may be conjugated with methyldithiobenzoic acid (MDTB). The free mercaptan group may then be used for conjugating with activated olefins. Thus, proteins, such as serum albumin, keyhole limpet hemocyanin, bovine β-globulin, or the like, may be conjugated to the peptide to provide for an immunogen to produce antibodies to the peptide for use in immunoassays, for affinity chromatography, or the like. Alternatively, the peptide can be bonded to another polypeptide by preparing a DNA sequence which has the peptide at the N-terminus, C-terminus or internal to the protein, so as to provide a fused protein which includes the binding peptide of interest. In this manner, fused proteins may be produced which have enzymatic activity, which enzymatic activity may be modulated by macromolecules, e.g., antibodies, binding to the peptide of interest. Thus, the peptides of the subject invention may be modified in a wide variety of ways for a variety of end purposes while still retaining biological activity.

The subject peptides may also be used in combination with antigenic peptides or proteins of interest to activate CTLs. Thus, the subject peptides may be bound to a protein, either directly or indirectly, so as to be able to present two epitopes to the CTL to which the CTL may bind and be activated. Of particular interest, is where the subject peptides may be bound to a liposome or a bilayer lipid membrane in conjunction with a peptide or protein providing the other determinant site.

Various techniques are available for joining a peptide or protein to a lipid, particularly a phospholipid to provide for the presence of the peptide or protein on the liposome surface. Phosphatidyl choline, phosphatidyl ethanolamine, or other lipid may be used with a bifunctional linking agent, such as MBSE, glutaraldehyde, methyldithiobenzoic acid, or the like. The formation of liposomes with conjugated proteins finds ample support in the literature, see, for example, U.S. Pat. Nos. 3,887,698; 4,261,975 and 4,193,983. The modified peptide or protein is combined with the lipids in an aqueous medium and sonicated to provide the desired liposomes. The liposomes may then be harvested and used in the ways indicated.

The subject peptides, by themselves, or in combination with other peptides or proteins, may be used for diagnosing the presence of CTLs which bind to a subject peptide or the combination of a subject peptide and other peptide or protein. In this manner, conjugates of the subject peptide and the antigenic peptide or protein can be prepared by employing linking agents as described previously. Alternatively, the subject peptide and the antigenic peptide may be bound to a solid surface, such as a particle, container surface, or the like. If desired, the subject peptide and antigenic peptide or protein may be conjugated to a particle or protein which is fluorescent. The binding of the particle or protein will allow for sorting and counting in a fluorescence activated cell sorter.

The subject peptides may be used for modulating CTL activity in a mammalian host, particularly inhibiting CTL activity. The modulating affect can be achieved in vivo or ex vivo, e.g. employing apheresis, where the patient's blood is withdrawn from the patient and circulated through a device in which the peptide is present in a physiologically acceptable medium to mix with the blood and inhibit CTL activity. Alternatively, the peptide may be used in the manner of affinity chromatography, so as to remove CTLs from the blood being circulated through the device. The peptides may be administered by any convenient means, depending upon the particular form in which the peptides are provided, e.g. monopeptide, oligomer peptides, the particular linking groups, and the like. Particularly, the peptides may be administered intravascularly, in either an artery or a vein, to provide for modulation of the CTL. The amount of the peptide which is administered, will vary with the form in which it is administered, the purpose for which it is administered, the frequency of administration, and the like.

Examples of inhibitory peptides are presented infra (see Examples 2 and 9), which are derived from both the $\alpha_1$ and $\alpha_2$ domain of HLA-A2. In each case the sequence of the inhibitory peptide correlates with the epitope specificity of the CTL. Moreover, as shown in Example 4, inhibition is mediated by an octapeptide, and occurs by peptide binding to the CTL and not the target cell (see Example 5). Since the inhibitory capacity of the individual peptides correlates with CTL specificity, it seems likely that these peptides inhibit by binding to the variable T cell receptor.

An example of a peptide which stimulates cytolysis of HLA-Class I bearing target cells by alloreactive CTL is presented in Example 10, infra. The simplest interpretation of the results in Examples 10–12 is that the HLA-A2/B17 specific CTL recognize the A2 56-69 peptide in the context of HLA-Aw69 as a restriction element.

The various activities of the peptides may be determined by appropriate assays. Inhibition of CTLs by peptides may be determined by employing CTL lines specific for a particular HLA in a target cell line carrying the target HLA. The target cell line is labeled, for example, with $^{51}Cr$. These cells are combined in an appropriate medium and the release of the label determined as indicative of the degree of cytolysis. The peptide may be added at the same time as the cells are brought together, may be incubated with the CTLs or may be incubated with the target cell to investigate the mode of action of the peptide.

Instead of using an exogenous marker, one may determine the release of serine esterase activity upon combining the CTLs and the target cells in conjunction with the peptide. The presence of serine esterase activity can be related to the release of granules.

As already indicated, the peptide may be present by itself, or in combination with an antigen thereby providing a different determinant site of interest. Depending upon whether only the subject peptide is included, or the peptide in combination with other peptides, activation or inhibition can be achieved. If irreversible inhibition is desired, the conjugate of the subject peptide with the antigen may be joined to a cytotoxic agent, joined to liposomes containing cytotoxic agents, or joined to a specific monoclonal antibody or immunoglobulin, whereby binding of the conjugate to the CTL will result in the complement mediated lysis of the CTL.

In addition, specific peptides may also serve to block differentiation of CTL, which blocking may be specific or non-specific. The subject peptides may also be used to modulate CTL activity, wherein modulation includes inhibiting cytolytic activity, where the inhibition may be reversible or irreversible. In some instances, the subject peptides may be used for determining the presence of particular sets or subsets of MHC-restricted CTLs.

These various capabilities may be achieved by combining cellular compositions comprising CTLs with the peptide in sufficient amount to provide the desired property. Where separation is desired, affinity columns, conjugated beads, e.g. magnetic beads, or other technique may be used, where the peptide-bound cells may be separated from other cells which are either not bound or non-specifically bound.

As indicated previously, particular peptides act on CTLs having a broad range of Class I MHC antigens. These compounds find particular application in protecting against transplantation rejection by providing for a regimen, where the peptides are administered at various times and in various periods, depending upon whether a bolus, slow release, a depot, continuous infusion or other form of dosage, the manner of administration, whether oral, parenteral, inhalation, or the like, the particular times chosen for the administration, the degree of difference between the transplantation antigens of the donor and recipient, and the like. The administration of the peptide may be prior to at and subsequent to the day of transplantation, or combination thereof. It is found that various regimens may be employed effectively, so that no particular regimen can be specifically defined. If the peptide is administered prior to the transplantation, administration should begin at least three days prior to the transplantation, preferably at least about five days, and more preferably at least about 7–20 days prior to the transplantation, while if the peptide is administered beginning at or after the transplantation, preferably administration is initiated within one day of the transplantation, preferably on the day of the transplantation, and may be administered during the grafting process. Usually there will be multiple administrations, usually not more than about 10, more usually not more than about 6, generally at least about 2, frequently ranging from about 2 to 6 administrations, where the administrations may be daily, alternating days, usually at not more than about 3 day, preferably not more than 2 day intervals. While multiple daily dosages may be given, it is found that a single dose per day will suffice. Therefore, overall the regimen will involve administrations during the period 20 days prior to the grafting operation and up to about 10 days subsequent to the grafting operation. There will usually be an initial dose beginning in the period −20 to +1 days, where (−) intends prior to the day of operation and (+) intends subsequent to the day of operation, with 0 being the day of operation. Preferably, the initial dose will be not earlier than 7 days prior to the operation, where the administration is primarily prior to the operation and not more than 1 day after the operation, where the initial dose is after the operation. The graft may also be bathed in a physiologically acceptable medium comprising the peptide, usually at a concentration associated with the dosage for the patient, when administered parenterally.

As part of the regimen, an immunosuppressant drug is also administered, generally at or subsequent to the transplant, either by itself, or in conjunction with the peptide, particularly where the peptide is administered after the transplantation. A subtherapeutic dose of the immunosuppressant compound is employed, where the immunosuppressant may be a single agent or a combination of agents, where the combination is below a subtherapeutic dosage. By subtherapeutic dosage is intended that in the absence of the peptide, the graft would be rejected in a majority of patients within 100 days, usually within 30 days, and more usually within 20 days. Various immunosuppressants are known, such as cyclosporin A, FK506, antibodies for plasma membrane proteins associated with graft rejection, such as antibodies to CD4, CD8, CD2, LFA-1, ICAM-1, CD28, and the like. The subtherapeutic dose will be not less than about 5% of the therapeutic dosage, usually not less than about 10%, more usually not less than about 25%, and usually not greater than about 75%, more usually not greater than about 60%. Where combinations are used, the subtherapeutic dosage is primarily directed to the drug(s) which have significant side effects, although there is a substantial interest in minimizing the effect on the immune system. In referring to a subtherapeutic dosage, is intended a bolus amount, since a direct comparison is difficult, where the subject regimen is terminated within a short period of the transplantation, the subject regimen may be daily or less than daily, and other regimens may involve repetitive daily administrations. Suffice it to say, that the subject regimen may be terminated within about 20 days, usually within about 10 days of the transplantation, as contrasted with other immunosuppressant regimens, which are for the life of the patient.

Generally, the amount of peptide administered will be in from about 0.1–50, more usually from about 1–25 mg/kg of host. This amount will be used for a peptide compound where the half life of the peptide compound is fewer than six hours, more particularly fewer than four hours and greater than about one hour. Dosages in the lower portion of the range and even lower dosages may be employed, where the peptide has an enhanced half-life or is provided as a depot, such as a slow release composition comprising particles, introduced in a matrix which maintains the peptide over an extended period of time, e.g. a collagen matrix, use of a pump which continuously infuses the peptide over an extended period of time at a substantially continuous rate, or the like.

Depending upon the time at which the peptide is administered prior to the transplantation, the immunosuppressant regimen may vary. For example, where the peptide is given at −7 and −1 day, a single subtherapeutic dosage of cyclosporin A was found to have insignificant protective capability, while administering cyclosporin A daily, 0–4 days, was shown to have protection. A regimen of administration of peptide on days −14, −12, −10 and −7 followed by cyclosporin A on days 0–4 after transplantation was also found to have substantial protective effect. Alternatively, by using a combined dosage of the peptide and a subtherapeutic dosage of cyclosporin A, on days 0–4 after transplantation, retention of the grafts was greatly enhanced.

The transplantation may involve any organ, such as a heart, kidneys, lung, eyes, liver, gut, vascular vessel, or other organ, where the organ is allogeneic or xenogeneic, particularly where one or more of the Class I MHC antigens are different in the donor as compared to the recipient.

In another application the subject peptides are found to bind to proteins of the plasma membrane which appear as 70 and 74 kD bands in gel electrophoresis. These bands can be observed by using peptides that have been conjugated at the amino terminus with polymethylene biotin, where the number of methylenes may range from about 2–15, more usually about 6–15. By then employing an avidin (includes streptavidin)—fluorescent conjugate, such as a phycobiliprotein, e.g. phycoerythrin or allophycocyanin, one can detect proteins separated in a gel employing a biotin labeled peptide, followed by contacting with the avidin-fluorescer conjugate and washing away non-specifically bound label. Alternatively, one may detect cells having the protein at the surface, by combining the cells with a peptide, washing away non-specifically bound peptide, combining the cells with the fluorescent conjugate, washing away non-specifically bound fluorescent conjugate and detecting the cells in a fluorescence activated cell sorter.

The 70 and 74 kD proteins may be isolated from the gel, further purified in sequence in accordance with conventional ways. Alternatively, the proteins may be used as immunogens for immunizing mammalian hosts for production of antiserum to the specific proteins. Alternatively, with an appropriate mammalian host, e.g. a mouse, one may remove the spleen, immortalize the splenocytes, and screen the resulting immortalized splenocytes for production of antibodies specific for the 70 and/or 74 kD proteins. These antibodies may then be used to inhibit binding to the 70 and/or 74 kd proteins present on the CTLs, so as to inhibit lytic activity of the CTLs.

The subject peptides, by themselves or as conjugates, may be prepared as formulations in pharmaceutically acceptable media, for example saline, PBS, aqueous ethanol and glucose, or as solid formulations in appropriate excipients, generally at a pharmacologically effective dose, the concentrations of which will be determined empirically in accordance with conventional procedures for the particular purpose. The formulations may include bactericidal agents, stabilizers, buffers, or the like. The amount administered to the host will vary depending upon what is being administered, the purpose of the administration, such as prophylaxis or therapy, whether inhibition or activation is desired, the state of the host, the manner of administration, the number of administrations and the interval between administrations, and the like. In order to enhance the half-life of the subject peptide or subject peptide conjugates, the peptides may be encapsulated, introduced into the lumen of liposomes, prepared as a colloid, or other conventional technique may be employed, which provides an extended lifetime of the peptides.

The following examples are offered by way of illustration and not by limitation.

EXAMPLES

Example 1

Preparation of Peptides Derived From HLA-A2

Four peptides were prepared by conventional synthetic methods using standard solid-phase methods. See Erickson & Merrifield in: *The Proteins* Vol. 2, 3rd edition (eds. Neurath, H. & Hill, R. L.) p. 255–527 (Academic Press, N.Y. 1970), which is hereby incorporated herein by reference. Three of the peptides had amino acids from the $\alpha_2$ domain and one of the peptides had amino acids from the $\alpha_2$ domain of a HLA-A2 antigen. The four peptides had the following compositions and designations:

| | |
|---|---|
| A2.56-69 G P E Y W D G E T R K V K A | (SEQ ID NO:8) |
| A2.94-112 T L Q R M Y G C D V G S D W R F L R G | (SEQ ID NO:5) |
| A2.98-113 M Y G C D V G S D W R F L R G Y | (SEQ ID NO:6) |
| Aw.68 98-113 M Y G C D V G S D G R F L R G Y | (SEQ ID NO:7) |

The designations indicate the major histocompatibility antigen from which the peptide is derived, and the position of the amino acids in the antigen.

Example 2

Inhibition of HLA-A2 Specific CTL by Peptides Derived from HLA-A2.98-113 and HLA-A2.94-112

Peptides prepared as in Example 1, i.e., those corresponding to HLA-A2.56-69, HLA-A2.94-112, HLA-A2.98-113, and HLA-Aw 68.98-113, were preincubated for 30 min. with $1-3\times10^3$ CTLs before addition of $10^3$ CPM of $^{51}$Cr-labeled B-lymphoblastoid target cells. The cytotoxicity assay was then performed as described by Clayberger et al., *J. Exp. Med.* (1984) 162:1709–1714; and Reiss et al., *Proc. Natl. Acad. Sci. USA* (1980) 77:5432–5436, which are hereby incorporated herein by reference.

In the first study, the CTL cell line was AJY, a long term $CD8^+$ CTL line specific for HLA-A2, and the target cell was the B-lymphoblastoid cell line JY (HLA-A2, B7). In the second study the CTL was PWSB, a bulk culture with reactivity against HLA-B17 and the target was FMB, which expresses HLA-A1, A32, B17. In each case the percentage of specific release obtained in the absence of peptide was determined. The lower amount of specific release in the second study potentially made cytolysis more sensitive to inhibition. Stocks of peptides at 1 mg/ml in PBS were diluted to give final concentrations in the assay as indicated in Table 1. As a control inhibitor, the monoclonal antibody PA2.6 which is directed against the monomorphic determinant of HLA-A, B, 6 molecules was used (Reiss et al., supra: McMichael, *J. Exp. Med.* (1980) 152:195s–203s). The peptides employed were A2.98-113, A2.94-112, Aw68.94 112 and A2.56-69. The following table indicates the results.

TABLE 1

| | | % Specific Lysis | | | |
|---|---|---|---|---|---|
| Concentration | µg/ml | A2.98-113 | A2.94-112 | Aw68.94-112 | A2.56-69 |
| Trial 1. | 160 | 0 | 3 | 52 | 51 |
| CTL = AJY | 80 | 4 | 20 | 45 | 38 |
| Target = JY | 40 | 18 | 35 | 63 | 61 |
| Trial 2. | 160 | 27 | 35 | 28 | 20 |
| CTL =PWSB | 80 | 29 | 32 | 30 | 27 |
| Target = FMB | 40 | 30 | 34 | 35 | 31 |

In the first case, the percentage specific release-obtained in the absence of peptide was about 54, while in the second case it was about 28.

The above results with CTL which are restricted by the HLA-A2 antigen, show inhibition of specific cytotoxicity. With CTL's not restricted by A2, lysis of random target cells occurs with the results approximating the standard specific release obtained in the absence of peptide. These results suggest that the tryptophan at position 107 may be critical. Peptide A2.98-113 and peptide Aw68.98-113 are homologous except for the substitution of glycine for tryptophan at this position; this substitution resulted in a loss of inhibition of cytolysis by HLA-A2 specific CTL.

The results of treatment of peptide A2.98-113 with different proteases, i.e., trypsin or chymotrypsin, allow the suggestion that arginine 108 is of importance, but that peptides 109–113 are not critical. The major sites of action of trypsin and chymotrypsin are Arg, Lys, and Trp, Phe, Tyr, respectively. Chymotryptic, but not tryptic, cleavage of the peptide reduced the inhibitory activity (results not shown).

Example 3

Effect of Specificity of CTL and Target Cell on Inhibition of Cytolysis Caused by HLA-Derived Peptides A number of different CTL cell lines were studied, where the specificity of the cell lines were varied. The results shown in Table 2 indicate that only where the CTL's and the target cells share A2 specificity do the A2-derived peptides provide inhibition.

sufficient to cause the inhibitory effect. A major decrease in the inhibitory effect occurs with loss of the cysteine at position 101. This loss may be due to the loss of disulfide cross-linking of two peptide molecules when cysteine 101 is absent.

Example 5

Locus of Action of Peptide A2.98-113

The locus at which peptide A2.98-113 interacts to cause an inhibitory effect on HLA-A2 specific CTL mediated cytolysis, i.e., with the CTL and/or with the target cell, was determined as follows.

The CTL ($1\times10^6$ CTL-A2) and/or the target cells ($^{51}$Cr-labeled JY target cells) were incubated with 100 μg of

TABLE 2

Specificity of CTL Tests for Inhibition by Peptides

| CTL | Specificity of CTL | Target Cell | Target Molecule | Inhibition of Lysis by Peptide | | | |
|---|---|---|---|---|---|---|---|
| | | | | A2.98-113 | A2.94-112 | Aw68.98-113 | A2.56-69 |
| Line AJY | A2 | JY | A2 | + | + | − | − |
| Line PJY | A2 | JY | A2 | + | + | − | − |
| Clone A20.1 | A2 | JY | A2 | + | + | − | − |
| Clone A1.10 | A2 | JY | A2 | + | + | − | − |
| Clone A19.1 | A2,Aw68,Aw69 | JY | A2 | + | + | − | − |
| Line PWSB | A2,B17 | JY | A2 | + | + | − | − |
| Line PWSB | A2,B17 | FMB | B17 | − | − | − | − |
| Clone AL8.1 | Aw68,Aw69 | LB | Aw68 | − | − | − | ND |
| Clone A15.1 | Aw69 | IDF | Aw69 | − | − | − | ND |
| Line CJY | Dr6 | Jy | DR6 | − | ND | − | − |
| Line CJY | Dr6 | DAUDI | Dr6 | − | ND | − | − |

The specificity of the CTL is based upon analysis of the pattern of killing on a panel of B lymphoblastoid cell lines and by patterns of inhibition with monoclonal antibodies. ND indicates not done. CTL used were from four different donors.

Example 4

Minimum Peptide Sequence Required for Inhibition of HLA-A2 Specific CTL

The minimum peptide sequence required for inhibition of cytolysis by HLA-A2 specific CTL was determined by examining the effect of size on the inhibition.

A series of peptides which started at positions 98–104 and ended at position 108 of HLA-A2 or HLA-Aw68 were synthesized. The effect of these peptides on cytolysis of JY cells (HLA-A2, B7, DR4,6) by seventeen different HLA-A specific lines or clones were tested. The HLA-A2 specific lines or clones were generated as described in Clayberger et al., supra. Peptides (200 mg/ml) were preincubated with $1-3\times10^3$ CTL for 30 minutes prior to addition of $10^3$ CPM of $^{51}$Cr-labeled target cells. The peptides were present throughout the cytotoxicity assay which was performed as described in Clayberger et al., supra, and in Krensky et al., Proc. Natl. Acad. Sci. USA 79:2365 (1982), which are hereby incorporated herein by reference. Peptides were prepared as stock solutions at 1 mg/ml in phosphate buffered saline and diluted in complete medium (MEN supplemented with 10% calf serum) to give the final concentration used.

The results on the inhibition of cytolysis by CTL-A2 is shown in FIG. 1A, where inhibition is expressed as (1-[specific cytolysis in the presence of peptide/specific cytolysis in the absence of peptide])×100.

As seen in the figure, peptide 104–108 did not inhibit, peptides 102–108 and 103–108 caused weak inhibition, and the remaining peptides caused good inhibition of cytolysis. Thus, an octapeptide comprising residues 101–108 was A2.98-113 for 30 min. at 37° C., or alternatively with the control peptide, Aw68.98-113. The sequences of these peptides are presented in Example 1. As an additional control, the cells were incubated with complete medium minus peptide. Following the incubation, the cells were washed three times in complete medium, and tested in a $^{51}$Cr-release assay (see Example 2).

Figure 2:
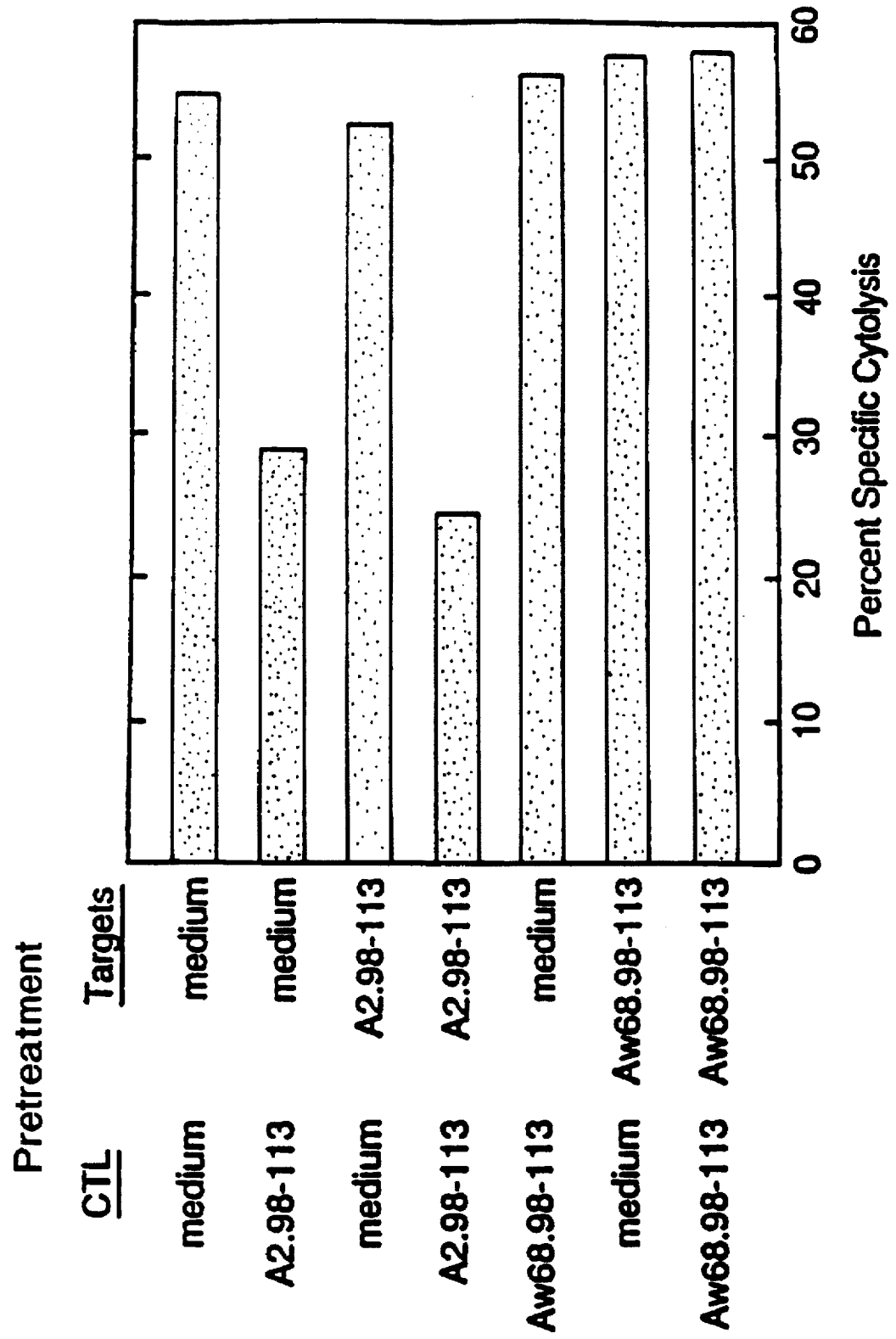
FIG. 2 shows the effect of pretreatment of CTL and of target cells on the inhibition of cytolysis by HLA-A2 specific CTL.

The results are presented in FIG. 2, where it may be seen that lysis was inhibited when the CTL, but not the target cells, were pretreated with A2.98-113. Inhibitory effects were not observed when CTL or target cells were pretreated with the control peptide, Aw68.98-113.

Example 6

Mechanism of Inhibition of CTL by A2.98-113 Effect on CTL Viability

To determine whether CTL were inhibited due to their autolysis induced by A2.98-113, either $^{51}$Cr-labeled CTL-A2 cells or unlabeled CTL-A2 cells were incubated with the peptide for 6 hours at 37° C. in complete medium. During the 6 hour incubation there was no detectable decrease in cell viability as judged by exclusion of trypan blue or by $^{51}$Cr-release (results not shown).

Example 7

Mechanism of Inhibition of CTL by A2.98-113 Effect on Release of Granules Containing Serine Esterase The effect of A2.98-113 on release of granules containing serine esterase during cytolysis of target cells by CTL was determined as follows.

The specificity of release was determined by incubating $3 \times 10^5$ HLA-A2 specific CTL with JY cells (HLA-A2; B7; Dr4,6) or IBW4 cells (HLA-A3; B35; DR1) for 2 hours in V bottom microtiter wells. The ratios of CTL:target cells were 1:0.01, 1:0.05, 1:0.10, 1:0.5, and 1:1. After the incubation, the plates were spun at 1000 RPM for 2 minutes, and the supernatant was assayed for serine esterase activity essentially as described in Young et al., Cell 47:183 (1986), which is hereby incorporated herein by reference. The reaction mixtures consisted of 20 µl of supernatant plus 200 µl of substrate ($2 \times 10^{-4}$M N-benzyloxycarbonyl-L-lysine thiobenzyl ester, $2.2 \times 10^{-4}$M nitrobenzoic 0.1M Tris-HCl, pH 8.0). After 30 min. at 37° C., the absorbance was determined at 410 nm. Total serine esterase activity was determined by substituting 0.01% Triton X-100 for stimulator cells. The results, shown in FIG. 3A, indicate that release of the granules occurred when the HLA-A2 specific CTL were incubated with JY cells (closed circles), but not when the HLA-A2 specific CTL were incubated with IBW4 cells (closed squares).

The effect of peptide A2.98-113 on release of granules containing serine esterase was determined in a similar fashion, except that the HLA-A2 specific CTL were preincubated with 100 µg of peptide, either A2.98-113 or Aw68.98-113, or with only complete medium, for 30 min. at 37° C. prior to the addition of JY target cells at ratios of CTL:target cells of 1:0.01, 1:0.05, 1:0.1, 1:0.5 and 1:1.

Figure 3:
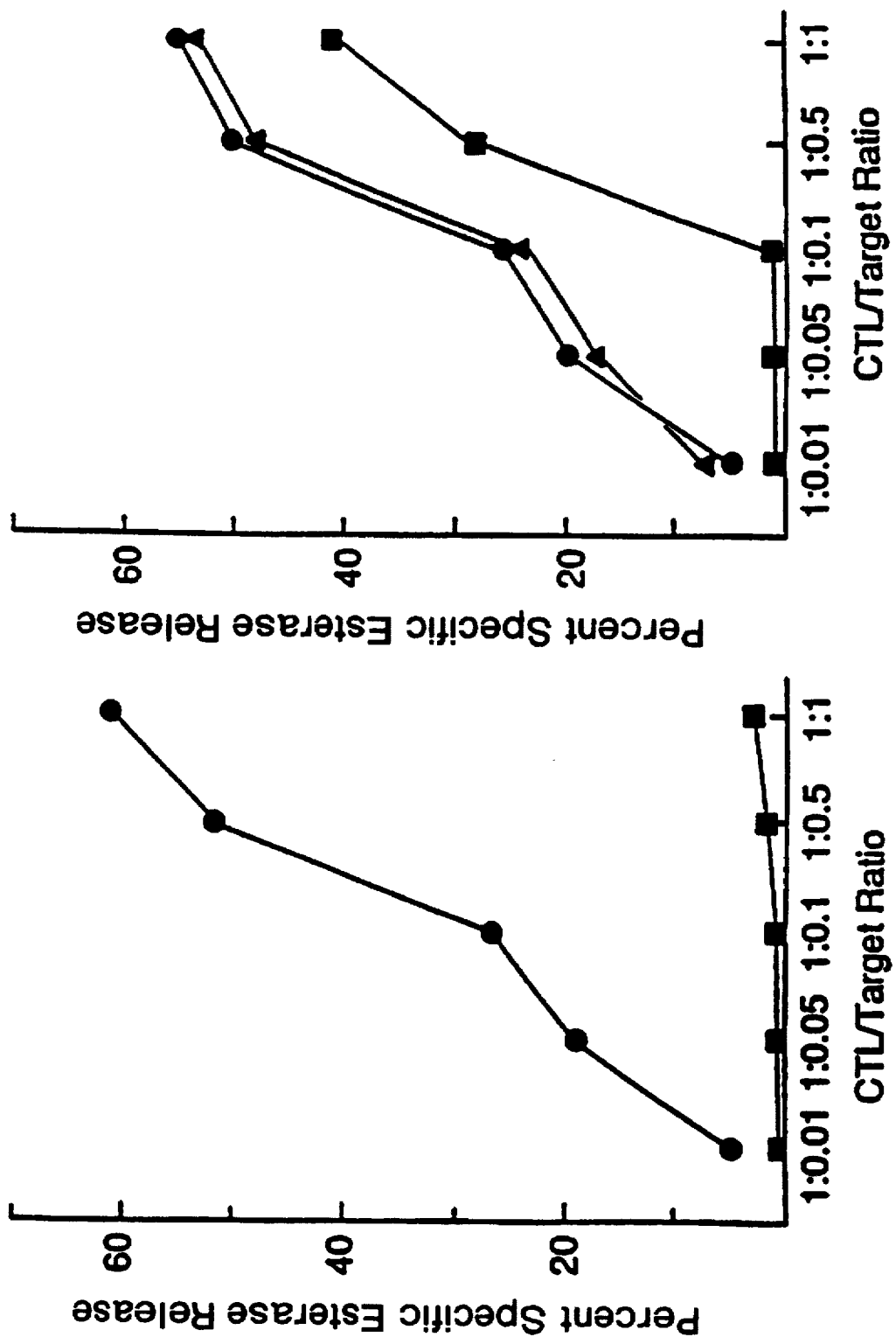
FIG. 3 shows the effect of peptide A2.98-113 on release of granules containing serine esterase during cytolysis of target cells by CTL.
Figure 5A:
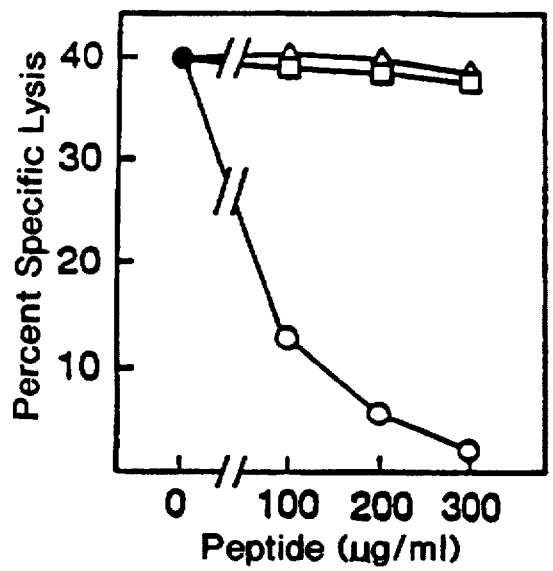
FIG. 5 shows the effect of peptides from different HLA-A2 epitopes on cytolysis of target cells by CTL of different specificities.
Figure 5B:
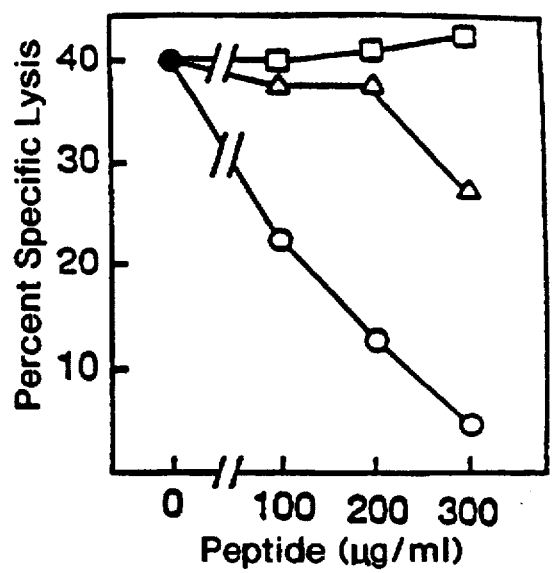
Figure 5C:
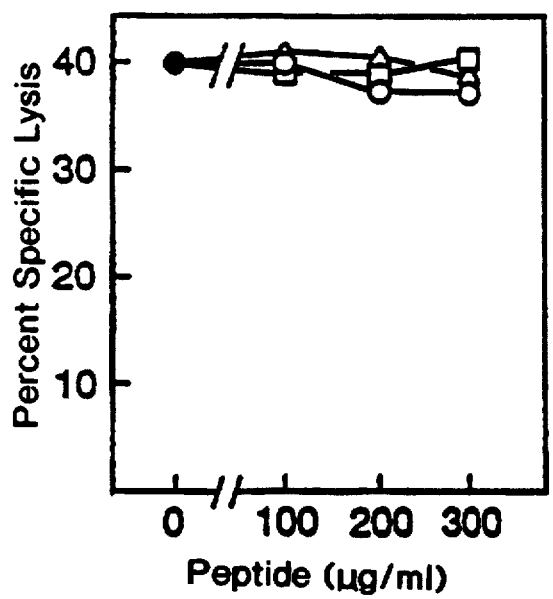
Figure 5D:
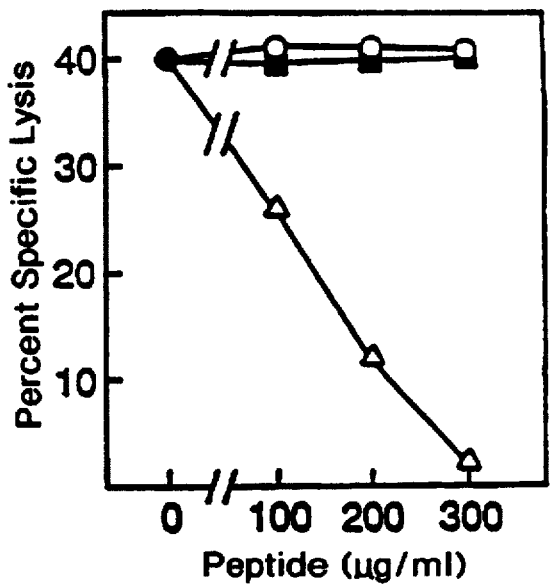

As seen in FIG. 3B, complete inhibition of esterase release was seen with 100 µg/ml of A2.98-113 at an effector-to-target ratio of 1:0.1 (closed squares). The control peptide Aw68.98-113 had no effect on esterase release (closed triangles), since release in this case was equal to that obtained with control cells preincubated with complete medium (closed circles).

These results, in conjunction with those in Example 5 indicate that the A2.98-113 peptide blocks events which occur early in T cell activation by binding directly to the CTL. This binding may be to the antigen receptor.

Example 8

Isolation of CTL Specific for the Epitope Shared by HLA-A2 and HLA-B17, for HLA-B17, and for HLA-A2

CTL with the various specificities were derived from the peripheral blood lymphocytes of a normal donor (HLA-A3; B7; DR6) essentially as described by Clayberger et al. (1985), supra. For CTL specific for the epitope shared between HLA-A2 and HLA-B17, the cells were stimulated in primary culture with the irradiated (10,000R) B-lymphoblastoid cell line Mag (HLA-A26,33; B17,51) and cloned using the SB cell line (HLA-A1,2; B17,44; DR2,6) as stimulators. CTL specific for B17 were derived from the same primary culture, but were cloned using the SH cell line (HLA-A3,w33; B7,17(w57)) as stimulators. HLA-A2 specific CTL were derived from cell stimulated in primary culture with the JY cell line and cloned using the Herluff cell line (HLA-A2; B12,35; DR4,7) as stimulators. The fine specificity of these CTL clones was assessed using a panel of 11 targets expressing HLA-B17, 8 targets expressing HLA-A2 and 15 targets with unrelated HLA molecules. Multiple clones of the desired specificities were obtained. An individual clone which caused cytolysis of both HLA-A2 type target cells and HLA-B17 type target cells was designated clone A2/B17. The cytolysis of target cells of clone A2/B17 was inhibited by antibody MA2.1. A second clone, which lysed all HLA-B17 target cells but no others was designated B17. A third clone, which lysed all HLA-A2 target cells but no others was designated CTL-A2.

The target specificity of clone A2/B17 and the finding that cytolysis by this clone was blocked by monoclonal antibody MA2.1 indicates that cells of clone A2/B17 recognize the epitope shared by HLA-A2 and HLA-B17.

Example 9

The Effect of Peptides from Different HLA-A2 Epitopes on Cytolysis of Target Cells by CTL of Different Specificities Examples 2-7, supra, have involved the effects of peptides derived from the region around tryptophan 107 in the $\alpha_2$ domain. This residue, which is on a bend between two strands of β pleated sheet (Bjorkman et al., (1987), supra), is critical for a major serologic epitope of HLA-A2. Salter et al., J. Exp. Med. 166:283 (1987); Layet et al., J. Immunol. 138:2197 (1987).

Another important epitope involves residues 62-65 of the α helical region of the $\alpha_1$ domain. Bjorkman et al., supra. This epitope was originally defined by the monoclonal antibody MA2.1 (McMichael et al., Hum. Immunol. 1:121 (1980)), and is shared by all known subtypes of HLA-A2 and HLA-B17 (Ways and Parham, Biochem. J. 216:423 (1983)). A comparison of the amino acid sequence of HLA-A2 and HLA-B17 and eight other HLA-A,B,C proteins showed that only the glycine residue at position 62 is unique, suggesting that this residue contributes to a shared determinant (Ways et al., J. Immunol. 137:217 (1986)).

Peptides derived from the above two regions were examined for their inhibitory effect on cytolysis of target cells by CTL with different HLA specificities, i.e., those of clone A2/B17, clone CTL-A2, and clone B17 (see Example 8, supra). CTL were incubated with the following peptides: A2.56-69, Aw68.56-69, A2.98-113, or Aw68.98-113.

Figure 4:
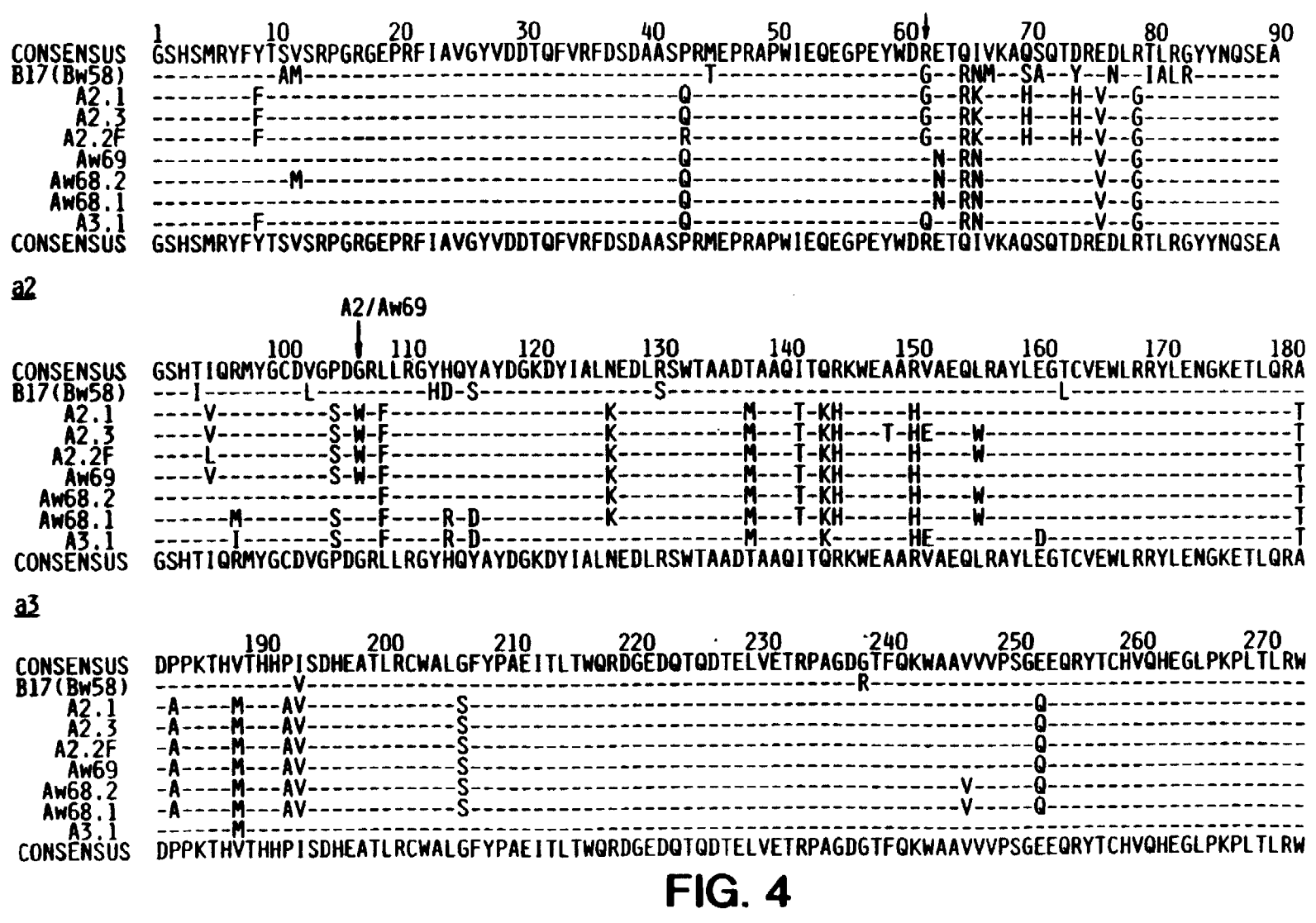

The epitopes studied and peptides used in the study are shown in FIG. 4, where the protein sequences in the three extracellular domains ($\alpha_1$, $\alpha_2$ and $\alpha_3$) of eight HLA-A,B molecules are shown using the standard one letter amino acid code. The sequence of HLA.Bw58 subtype of HLA-B17 is from Ways et al., J. Biol. Chem. 260:11924 (1985), that of HLA-A3.1 is from Strachen et al., EMBO J. 3:887 (1984), and the remaining sequences of the HLA-A2/28 family are from Holmes et al., J. Immunol. 139:936 (1987). Peptides A2.56-69 and Aw68.56-69, and A2.98-113 and Aw68.98-113, which are derived from $\alpha_1$ and $\alpha_2$, respectively, are indicated by cross-hatching. The two residues found to be critical for the epitopes shared by subtypes of HLA-A2 and HLA-B17 (glycine 62) and subtypes HLA-A2 and HLA-Aw69 (tryptophan 107) are indicated by stippling and the vertical arrows. The consensus sequence is derived from a total of 23 HLA-A,B,C sequences.

The CTL were incubated with peptides at concentrations of 100 µg/ml, 200 µg/ml, or 300 µg/ml. Control samples were incubated in the absence of peptide. The final molar concentrations of peptides used in the assay at 100 µg/ml were $4.9 \times 10^{-5}$M for A2.98-113; $5.2 \times 10^{-5}$M for Aw68.98-113; $5.9 \times 10^{-5}$M for A2.56-69; and $5.9 \times 10^{-5}$M for Aw68.56-69. The CTL cells were incubated with the peptides for 20 min. prior to the addition of $10^3$ $^{51}$Cr-labeled T7529 cells (HLA-Aw33; B17(w58); DR6) or JY cells (HLA-A2; B17; DR4,6). In all cases, the effector-to-target ratios were 1:1.

The results on cytotoxicity, as measured by $^{51}$chromium release from the target cells, is shown in FIG. 5. FIGS. 5A and 5B show the results of the effects of the peptides on cells of clone A2/B17; FIG. 5C shows the effects on cells of clone B17, and FIG. 5D on CTL-A2. The peptides are indicated as follows: (open circles) A2.56-69; (open squares) Aw68.56-69; (open triangles) Aw.98-113; and (closed squares)

Aw68.98-113. Peptide A2.56-69, which encompasses the shared serologic epitope, specifically inhibited the killing of both HLA-A2 and HLA-B17 expressing target cells by clone A2/B17 cells. In contrast, this peptide had no effect upon the lysis of HLA-B17 expressing cells by clone B17 cells. Clone A2/B17 cells were not inhibited by a peptide derived from residues 56–69 of HLA-Aw68.1, or by a series of unrelated peptides. The A2.98-113 peptide did not affect the lysis of HLA-B17 expressing targets by clone A2/B17 cells, but some inhibition was observed at high concentrations with HLA-A2 expressing targets. This difference indicates that the epitopes of HLA-A2 and HLA-B17 recognized by clone A2/B17 cells are not precisely the same.

These results show that the capacity of peptides to inhibit alloreactive CTL is not restricted to the region involving residues 101–108 of the $\alpha_2$ domain, and that they may be derived from a second epitope of HLA-A2.

The discrepancy of the results achieved with peptide A2.56-69 using clone A2/B17, and those with the PWSB cell line (see Table 2) with respect to the inhibitory effect of this peptide may be explained by the polyclonal nature of the PWSB cells. That is, the PWSB line probably is a mixture of CTL's including individual clones specific for HLA-A2 or HLA-B17.

Example 10

Sensitization of Target Cells to CTL caused by a HLA-A2 Derived Polypeptide

Figure 6:
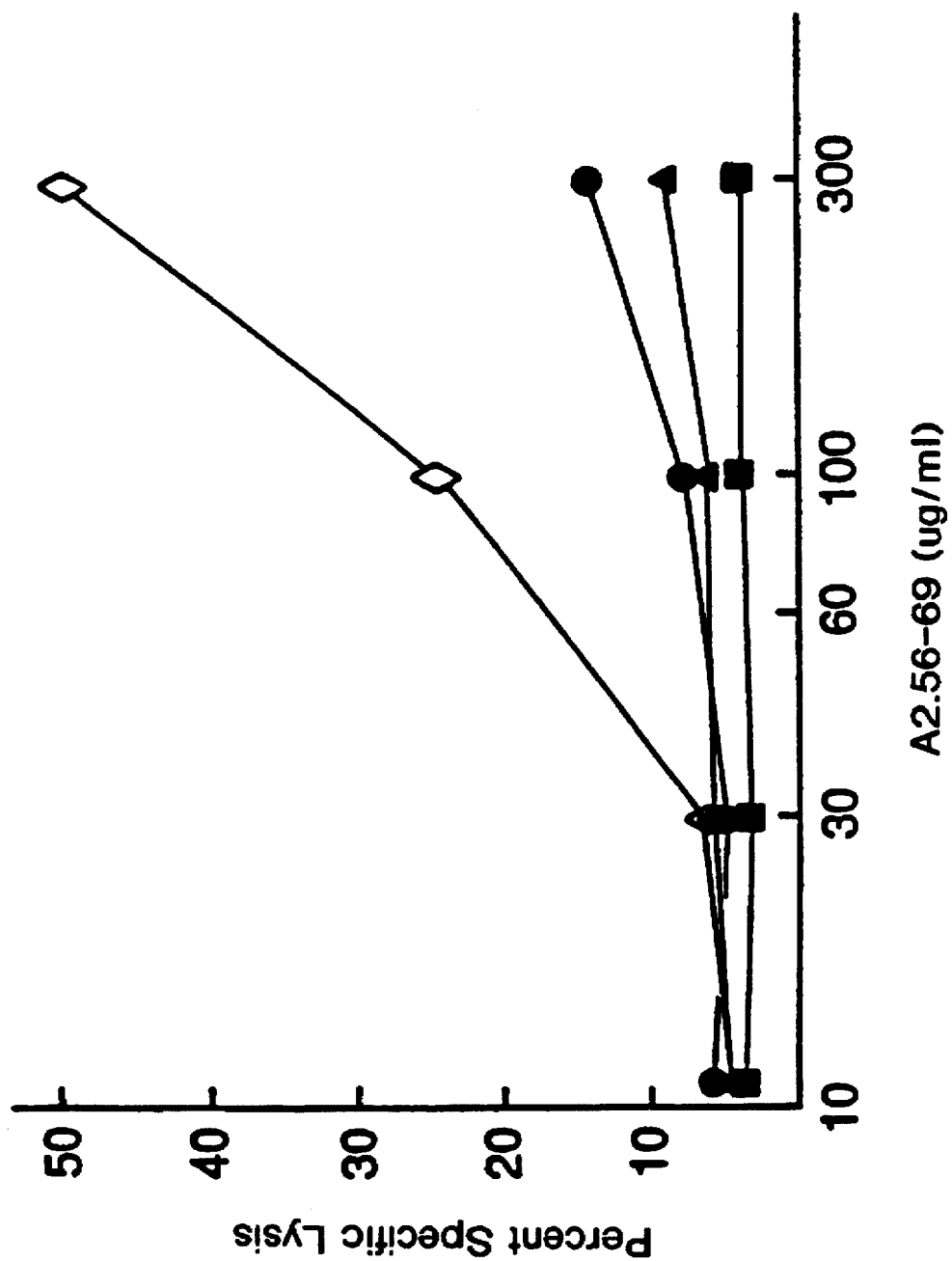
FIG. 6 shows the sensitization of an HLA-Aw69 target cell to cytolysis by clone A2/B17 cells caused by peptide A2.56-69.

Clone A2/B17 was incubated with peptide A2.56-69 and $^{51}$Cr-labeled target cells at an effector-to-target ratio of 5:1 for 5 hours, after which $^{51}$chromium released was measured. The concentrations of peptide were 10, 30, 100, and 300 µg/ml. The results of the effect of peptide on the percent of specific lysis of the target cells by clone A2/B17 cells are presented in FIG. 6. The target cells were: (closed square), IBW4 (HLA-A3; B35; DR1); (closed triangle), LB (HLA-Aw68.1; B40, DR6); (closed circle), Pally (HLA-Aw68.2, 26; B14,38; DR1,4), or (open diamond), IDF (HLA-Aw69, 26; B15, 38, DR5).

In the absence of peptide, clone A2/B17 cells do not lyse targets expressing HLA-Aw69, HLA-Aw68.1, and HLA-Aw68.2 (data not shown). The inability of clone A2/B17 cells to lyse these targets is due to the differences in the critical residues around position 62 from those found in HLA-A2 and HLA-B17. However, when peptide A2.56-69 was included in the cytotoxicity assay, there was significant lysis of HLA-Aw69 expressing targets by A2/B17 cells (FIG. 5). In contrast, targets expressing HLA-Aw68.1, HLA-Aw68.2, or the unrelated HLA-A3 molecule were not lysed.

Lysis of HLA-Aw69 cells by clone A2/B17 cells in the presence of peptide A2.56-69 was blocked by monoclonal antibody DR11-351, which only binds to the HLA-Aw69 of the target cell. In contrast, the monoclonal antibody MA2.1 did not inhibit lysis (results not shown). MA2.1 binds to the epitope of HLA-A2 and HLA-B17 formed by residues 56–69, but does not bind to the HLA-Aw69 or peptide A2.56-69. These results demonstrate the involvement of the HLA-Aw69 molecule in the sensitization by peptide A2.56-69.

The addition of A2.98-113 peptide to B cell lines which do not express HLA-A2 did not cause sensitization to lysis when target cells expressing a variety of HLA molecules were used. This was true even though a wide range of peptide concentrations (0.1 to 300 µg/ml were used.)

In binding A2.56-69, the HLA-Aw69 molecule is able to present an epitope that mimics the native structure of HLA-A2. That HLA-Aw69 but not other members of the HLA-A2/28 family can be sensitized is of interest. HLA-Aw69 is a recombinant molecule having $\alpha_1$ derived from HLA-Aw6B and $\alpha_2$ and $\alpha_3$ derived from HLA-A2.1 (Holmes and Parham, *EMBO J.* 4:2849 (1985)). Thus, HLA-2.1 and HLA-Aw69 differ by only 6 amino acids, all residing in the $\alpha_1$ domain and three of which are present in the A2.56-69 peptide.

Example 11

Locus of Peptide Interaction in Sensitization

To assess whether sensitization resulted from peptide interaction with the CTL or the target, cells were pretreated with A2.56-69, washed and then tested for cytolysis. More specifically, 1×10$^6$ clone A2/B17 cells or $^{51}$Cr-labeled IDF (HLA-Aw69,26; B18,38; DR5) were incubated with 100 µg of peptide or medium for 30 min. at 37° C., washed three times, and cytotoxicity as determined by $^{51}$chromium release was measured.

Figure 7:
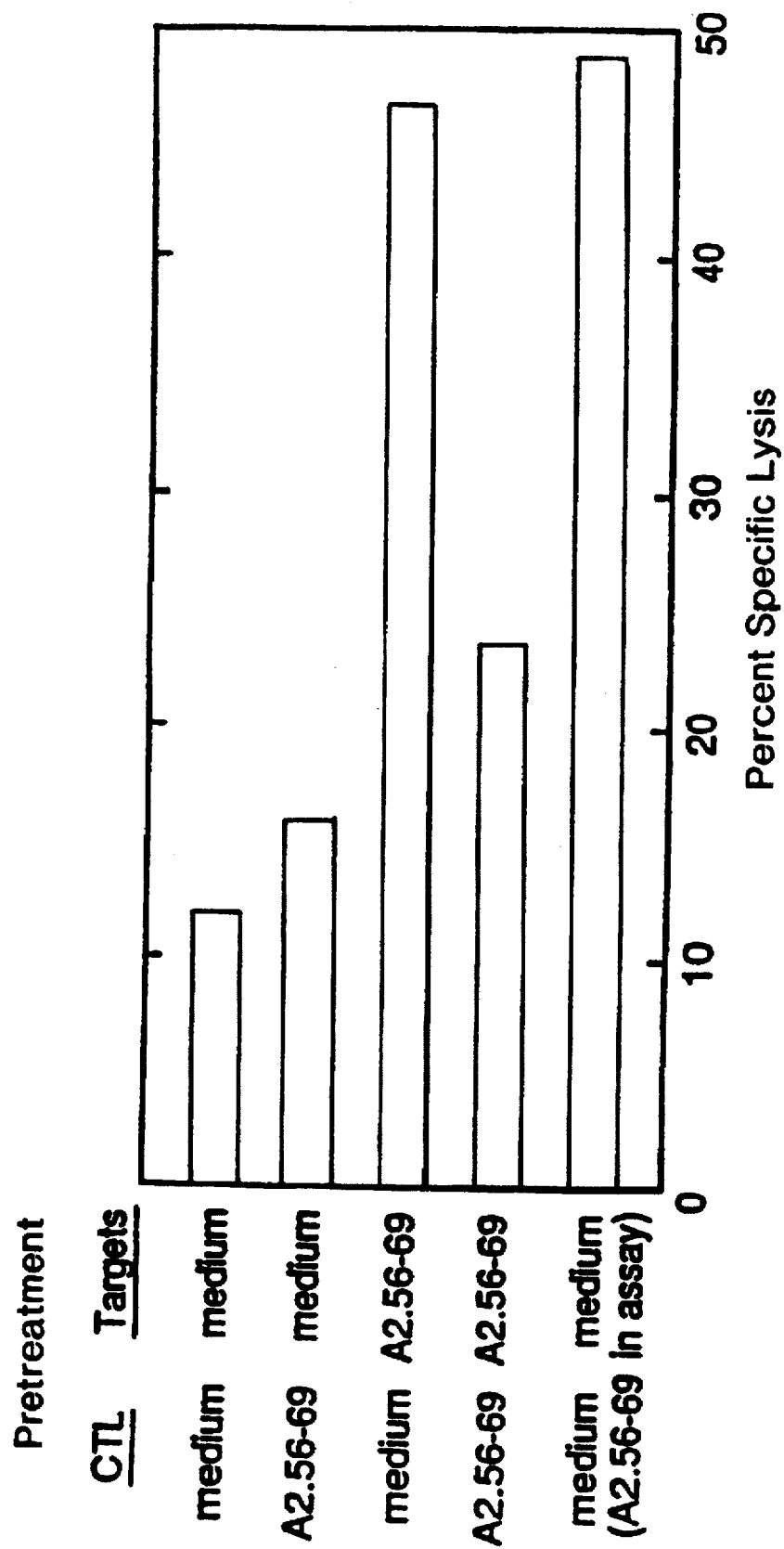
FIG. 7 shows the effect on sensitization of incubating target cells or clone A2/B17 cells with peptide A2.56-69.

As seen from the results presented in FIG. 7, target cells expressing HLA-Aw69 were lysed when the targets, but not the CTL, were pretreated with A2.56-69.

Example 12

Effect of Peptide A2.56-69 on Release of Granules Containing Serine Esterase

The effect of peptide A2.56-69 on the release of granules containing serine esterase during co-culture of A2/B17 cells with HLA-Aw69 expressing cells may be performed essentially as described in Example 7, supra, except that the CTL are from clone A2/B17, the target cells are those expressing HLA-Aw69, and the cells are co-cultured in the absence or presence of peptide A2.56-69.

Example 13

Effect of a Variety of HLA Peptides of Amino Acids 60–84 and HLA-B 2702/05.145-169 on Lysis These peptides were synthesized and had the following sequence:

| | | |
|---|---|---|
| HLA-B2702.60-84 | WDRETQICKAKAQTDRENLRIALRY | (SEQ ID NO:26) |
| HLA-B2705.60-84 | WDRETQICKAKAQTDREDLRTLLRY | (SEQ ID NO:27) |
| HLA-Bw46.60-84 | WDRETQKYKRQAQTDRVSLRNLRGY | (SEQ ID NO:20) |
| HLA-Bw62.60-84 | WDRETQISKTNTQTYRESLRNLRGY | (SEQ ID NO:11) |
| HLA-A2.1.60-84 | WDGETRKVKAHSQTHRVDLGTLRGY | (SEQ ID NO:12) |
| HLA-B2702/05.145-169 | RKWEAARVAEQLRAYLEGECVEWLR | (SEQ ID NO:28) |
| HLAB38.6084 | WDRNTQICKTNTQTYRENLRIALRY | (SEQ ID NO:29) |

The effect of the above sequences on lysis of long-term CTL specific for HLA-A2, -B2705, -Bw46, -Bw62, and -Cw4 was determined as described in Examples 2 and 3, and also included CTL specific for HLA-B27 and the HLA-Cw4.

None of the peptides inhibited or enhanced lysis with the exception of the B2702.60-84 peptide. This peptide blocked lysis by all CTL, regardless of their HLA specificity. This effect was due to interaction with the CTL and not the target cell as shown by pre-treatment experiments (as in Example 5).

These peptides were tested for effects on the differentiation of CTL from CTL precursors in limiting dilution assay. The procedure was modified from Skinner and Marbrook (*J. Exp. Med.* 143:1562; 1976) as follows: PBL from normal HLA-typed donors were purified over Ficoll-Hypaque and co-cultured in round bottom microtiter wells with irradiated (10,000 R) EBV transformed B-lymphoblasts expressing the HLA allele of interest. Responder PBL were added at 3000, 6000, 10000 and 30000 cells per well while stimulators were added at 6000 cells per well. 20-4 replicates were set up for each concentration of responder cells in RPMI-1640 medium supplemented with 10% fetal bovine serum plus L-glutamine. Plates were incubated for six days in a 5% $CO_2$/95% air humidified incubator at which time the contents of each well were mixed by pipetting five times with a multi-channel pipette. Fifty microliter aliquots were transferred to the V-bottom microtiter wells to which 1000 $^{51}$Cr labeled targets of known HLA type were then added. Lysis was determined in a four-hour cytotoxicity assay (Example 2). Wells were designated positive if specific lysis was >10%. CTL precursor frequency was determined by linear regression analysis using a computer program.

The B2702.60-84, Bw46.60-84 and Bw62.60-84 peptides all blocked the differentiation of CTL, whereas the other peptides had no effect.

| Effect of Peptides Corresponding to HLA Regions on CTL Precursor Frequency as Determined by Limiting Dilution Analytis | |
|---|---|
| Peptide | 1/CTL Precursor Frequency |
| B2705.60-84 | 164,245 |
| B2702.60-84 | 3,349,990 |
| B38.60-84 | 3,334,937 |
| A2.160-84 | 164,245 |
| B46.60-84 | 2,995,400 |
| B62.60-84 | 2,995,400 |
| B27.145-169 | 164,245 |

PBL from a normal donor (HLA-A3; B-7, 38; Cw4; DR4,6) were cultured with JY (HLA-A2; B7; DR4,6) or HOM2 (HLA-A3; B27) in the presence of 10–100 µg/ml peptide. After 6 days, lysis was tested on $^{51}$Cr-labeled CIR cells expressing either HLA-A2.1 or HLA-B2705. Results are shown for HLA-A2 specific lysis but similar results were obtained for HLA-B27 specific lysis.

The effect was not allele specific since the differentiation of CTL specific for a number of different HLA molecules was inhibited. None of the peptides affected Class II restricted responses, including mixed lymphocyte responses and mitogen induced proliferation.

PBL from normal donors were cultured at $5\times10^5$ cells/round bottom microtiter well in RPMI-1640 supplemented with 10% fetal bovine serum and L-glutamine. Cultures were supplemented with either $5\times10^3$ irradiated (10,000 R) EBV transformed B lymphoblasts or 10 µg/ml phytahemagglutinin P (PHA-P). Cells were incubated at 37° C. for 3 days for PHA-P and 5 days for alloantigen at which point $^3$H-thymidine was added (2 µCi/well). After 16 hours wells were harvested and $^3$H-thymidine incorporation determined by scintillation counter.

Example 14

Effect of Truncated Sequences on Lysis and Differentiation

Since the B2702.60-84 and B2705.60-84 peptides differed by only 3 amino acids, additional peptides were prepared to investigate the effect of these differences. Three additional peptides were synthesized (SEQ ID NO:13 through SEQ ID NO:15):

| HLA-B2702.75-84 | RENLRIALRY |
|---|---|
| HLA-B2705.75-84 | REDLRTLLRY |
| HLA-B2702/05.60-69 | WDRETQICKA |

Following the procedures described in Example 13, the peptide corresponding to residues 60–69 of HLA-B2702/05 had no effect on the assays described above. The peptide corresponding to residues 75–84 of HLA-B2702 blocked all Class I specific CTL responses, whereas the peptide corresponding to the same region of HLA-B2705 did not.

To determine which residue(s) mediated the inhibitory effects, 3 more peptides were synthesized in which single amino acid changes were introduced at residues 77, 80 and 81 to convert the B2702 sequence into the B2705 sequence at that position. The B2702.75-84(D) and B2702.75-84(L) peptides still blocked lysis by existing CTL and differentiation of pre-CTL while the B2702.75-84(T) peptide had no inhibitory activity. Thus, the isoleucine at position 80 is required for inhibition.

| HLA-B2702.75-84(D) | REDLRIALRY (SEQ ID NO:30) |
|---|---|
| HLA-B2702.75-84(T) | RENLRTALRY (SEQ ID NO:31) |
| HLA-B2702.75-84(L) | RENLRILLRY (SEQ ID NO:32) |

It was also found by the following assay that B2702.60-84, B38.60-84 and B2702.75-84 when pre-bound to plastic caused cells to bind. None of the other peptides were found to have this effect. However, when the B2702.60-84 peptide was conjugated to bovine serum albumin or to beads via the cysteine at residue 67, the blocking effect and the ability to bind cells to plastics were lost.

The plastic binding procedure was as follows: peptide (100 µg/ml) was dissolved in PBS and 50 µl was added to round bottom microtiter wells or 5–10 µl to petri dishes. After 60 minutes at 37° C. or overnight at 4°, the solution was removed and the plates washed twice in RPMI-1640 supplemented with 10% fetal bovine serum. Cells were added and incubated at 4° for 30 minutes. Binding to petri dishes was determined by inspecting the dishes under a microscope following gentle agitation. Binding to microtiter wells was determined after centrifugation at 500 rpm for 3 minutes. Cells which did not bind formed a small pellet at the bottom of the well whereas cells that did bind did not form a pellet.

Binding occurred equally well at 4°, 25°, or 37° and was not dependent on exogenously added divalent cations since binding was observed in medium containing EDTA. However, if cells were preincubated with 1% $NaN_3$ or fixed with paraformaldehyde, no binding was observed, indicating that viable cells and most likely generation of ATP were required.

Example 15

Preparation of Peptide Oligomers

A number of peptide oligomers were prepared involving the B2702.75-84 sequence and mutants thereof, where the isoleucine in the sequence was substituted with threonine. The oligomers involved dimers having a "inverted dimer peptide" of the pair and sequence (84-75/75-84), a tail-to-head or "backwards" sequence (84-75/84-75) and the peptide covalently attached to a polylysine having eight branches (MAP$_8$02.75-84).

The following table indicates the various sequences:

TABLE 3

| | |
|---|---|
| B2702.75-84 | RENLRIALRY (SEQ ID NO:13) |
| 02.84-75/75-84 | YRLAIRLNERRENLRIALRY (SEQ ID NO:33) |
| 02.84-75(T)/75-84 | YRLATRLNERRENLRIALRY (SEQ ID NO:34) |
| 02.84-75/75-84(T) | YRLAIRLNERRENLRTALRY (SEQ ID NO:35) |
| 02.84-75(T)/75-84(T) | YRLATRLNERRENLRTALRY (SEQ ID NO:36) |
| 02.84-75/84-75 | YRLAIRLNERYRLAIRLNER (SEQ ID NO:37) |
| 02.60-84 | WDRETQICKAKAQTDRENLRIALRY (SEQ ID NO:26) |
| 02.70-84 | KAQTDRENLRIALRY (SEQ ID NO:38) |
| MAP$_8$02.75-84 | |
| B7.75-84 | RESLRNLRGY (SEQ ID NO:39) |
| B7.84-75/75-84 | YGRLNRLSERRESLRNLRGY (SEQ ID NO:40) |
| MAP$_8$B7.75-84 | |

MAP is a multiple antigenic peptide that is composed of a branched lysine backbone to which a peptide is covalently attached. We have used an eight branch lysine.

The binding assay was based on peptides that had been conjugated at the amino terminus with —(CH$_2$)$_{12}$-biotin. A streptavidin-phycoerythrin conjugate was then used for detection in a fluorescence activated cell sorter (FACS). Precipitation was also based on the use of the biotinylated compounds, where a streptavidin-agarose was used to isolate the proteins to which the subject peptides were bound. (The procedure followed the recommendation of the supplier, Pierce). The calcium influx determination was performed in accordance with the procedure described by Grynkiewicz, et al. 1985, J Biol Chem 260(6):3440–50. It was found that in both the binding detected using the FACS and the precipitation of the proteins, the binding could be inhibited with unconjugated peptide.

TABLE 4

| Peptide | Inhibition of in vitro immune assays | Binding on FACS | Ca++ influx | Precipitation of 70 and 74 kD proteins |
|---|---|---|---|---|
| B2702.75-84 | + | ND | – | ND |
| 02.84-75/75-84 | +++ | ++ | ++ | + |
| 02.84-75(T)/75-84 | +/– | +/– | +/– | +/– |
| 02.84-75/75-84(T) | – | – | – | – |
| 02.84-75(T)/75-84(T) | – | – | – | – |
| 02.84-75/84-75 | ++ | + | ND | ND |
| 02.60-84 | ++ | + | – | ND |
| 02.70-84 | – | – | – | ND |
| MAP$_8$02.75-84 | ++ | ND | ++ | ND |
| B7.75-84 | – | – | – | – |
| B7.84-75/75-84 | – | – | – | – |
| MAP$_8$B7.75-84 | – | ND | – | ND |

Example 16

Allograft protection in a rat model
Materials and Methods
Animals

Adult male, specific pathogen free ACI (RT1$^a$), PVG (RT1$^c$), Brown Norway (BN) (RT1$^n$), and Lewis (Lew) (RT1$^1$) rats, weighing 200–250 grams, were used in these studies. Animals were purchased from Bantin and Kingman, Fremont, CA (PVG) or Charles River, Boston, MA (ACI, BN and Lew). ACI rats served as recipients of heart or skin allografts from BN or Lew donors. Animals were maintained in the Falk Cardiovascular Research Building under standard conditions according to institutional guidelines.

Peptides

Peptides were synthesized at the Protein and Nucleic Acid Facility, Beckman Center, Stanford University School of Medicine, or by Multiple Peptide Systems (San Diego, Calif.) by an automated peptide synthesizer using Fmoc chemistry. Peptides were purified by preparative reverse phase HPLC and shown to be >98% homogeneous by analytical reverse phase HPLC. Amino acid content was confirmed by amino acid analysis.

Lymph Node Proliferation Assay

ACI or PVG rats (200 g) were injected intravenously with 2 mg of B7.75-84 dissolved in saline on day 0. On the indicated days thereafter, the left rear footpads of 3 animals were injected with 5×10$^6$ splenocytes from a syngeneic donor and the right rear footpads with 5×10$^6$ splenocytes from an allogeneic Lew donor (Moeller et al. 1993, Transplantation, 55:650). Seven days after the footpad injection, the animals were sacrificed and the popliteal lymph nodes removed. A single cell suspension was prepared, and the cell number determined using a hemocytometer.

Limiting Dilutions Assay for CTL Precursors

Limiting dilution analysis was carried out essentially as described (Moeller et al. 1993, supra; Skinner and Marbrook. 1976. J. Exp. Med. 143:1562). Briefly, spleens were removed from naive animals or from animals that had received an allograft a minimum of 60 days earlier and then teased into a single cell suspension. Responder cells were plated from 1000 to 40,000 cells per well (24 replicates per concentration) into round bottom microtiter wells in RPMI 1640 supplemented with 10% fetal bovine serum (Hyclone, Logan, Utah), 2 mM L-glutamine, 5×10$^{-5}$M β-mercaptoethanol, 100 U/ml penicillin, 100 μg/ml streptomycin, 20% supernatant from Concanavalin A activated rat spleen cells, and 50 μM α-methyl mannoside. Then, 5×10$^5$ irradiated (2000 rads) stimulator cells were added to each well and plates were incubated in a humidified CO$_2$ incubator. After 5 days, aliquots were removed and tested for lysis of $^{51}$Cr-labeled Concanavalin A activated blasts. Aliquots of supernatant were counted in a gamma counter and CTL precursor frequency determined by linear regression (Skinner and Marbrook. 1976, supra). Wells were considered positive if specific release was >10%.

Organ Transplantation

Vascularized cardiac allografts were heterotopically transplanted into the abdomen of recipient rats using a modification of the technique of Ono and Lindsay (Ono and Lindsey. 1969. J. Thorac. Cardiovasc. Surg. 57:225). Abdominal allografts were palpated on a daily basis to assess graft function, and rejection was deemed complete when palpable ventricular contractions ceased. Full thickness skin grafts were performed using a modification of the technique described by Billingham and Medawar (1951. *J. Exp. Biol.* 28:385). Both donor and recipient were shaved and the donor skin was cut in standard 2×2 cm pieces and subdermal fat was surgically removed. Multiple grafts were obtained from a single donor, preserved in cold saline and transplanted on the same day. A piece of skin the same size as the donor graft was removed from the flank of the recipient and any loose connective tissue was surgically removed from the fascia. The allograft was then fashioned to the recipient fascia with a 4-0 vicryl suture. One layer of rough gauze and eight layers of fine gauze sponge were sewn to the recipient skin and fascia around the graft using a 2-0 vicryl suture, securely immobilizing the donor skin to the recipient fascia and allowing the graft to be revascularized. On post-operative day 6 the dressing was removed and the allograft was then inspected for evidence of rejection on a daily basis. Rejection was manifested by erythema, continuous serous exudation, ulceration or allograft necrosis.

Immunosuppression

Cyclosporin A (CsA, Sandoz Pharmaceuticals Corporation, Base, Switzerland) dissolved in olive oil was given orally through a gavage tube at the indicated dose. Peptides were dissolved in water or saline and given intravenously or by gavage as indicated.

Statistical Analyses

Student t-tests were calculated using the Graphpad InStat statistics program to compare allograft survival in different groups. Differences were considered significant if the p value was <0.05.

Results

Cells from rats immunized in vivo with a single dose of peptides are unresponsive to allogeneic challenge in vivo or in vitro.

Initial studies showed that both the B7.75-84 and B2702.75-84 peptides, but neither the A2.75-84 peptide nor a peptide corresponding to the same residues from a rat MHC class I molecule, RT1$^a$, blocked the differentiation of rat splenocytes into allospecific CTL in vitro (not shown). Therefore, we tested whether splenocytes obtained from rats treated with the peptides in vivo could differentiate into CTL ex vivo. In preliminary studies, the half-life of the B7.75-84 peptide was determined to be 2–3 hours in rats. Thus, we elected to administer 2–20 mg peptide (6–60 mg/kg) per dose, an amount that is comparable to the dose of the undecapeptide CsA, (10–20 mg/kg). PVG (RT1$^c$) or ACI (RT1$^a$) rats were treated with a single intravenous injection of saline or 2 mg of A2.75-84, B7.75-84, B2702.75-84, or RT1$^a$.75-84 peptide. Their spleens were removed on different days after peptide treatment, cultured under limiting dilution conditions for 5 days with Lew (RT1$^l$) stimulator cells, and assayed for lysis of $^{51}$Cr-labeled Lew blasts (Table 5). The precursor frequency of Lew specific cells in splenocytes isolated from PVG rats treated with either saline, the A2.75-84 peptide, or the RT1$^a$.75-84 peptide was approximately 1 in 55,000, independent of the day on which the spleen was removed. The same frequency was found in splenocytes from animals that had been treated with either the B7.75-84 or B2702.75-84 peptide on the day of splenectomy or 24 hours earlier. However, splenocytes obtained from animals treated with the B7.75-84 or B2702.75-84 peptide 7 or 10 days prior to splenectomy showed an 8-10 fold decrease in the precursor frequency of Lew specific CTL.

TABLE 5

CTL precursor frequencies in splenocytes isolated from rats following injection of saline or α, alpha helix peptide.

| Injection (days) | Time after Peptide [CTL precursor frequency]$^{-1}$ | | | | |
|---|---|---|---|---|---|
| | Saline | A2.75-84 | RT1A.75-84 | B7.75-84 | B2702.75-84 |
| 0 | 54,631 | 55,467 | 56,583 | 55,467 | 54,631 |
| 1 | 55,467 | 55,467 | 54,631 | 55,467 | 54,631 |
| 7 | 56,583 | 54,631 | 55,647 | 567,004 | 465,572 |
| 10 | 54,631 | 55,467 | 56,583 | 634,983 | 468,071 |

PVG rats (2/group) were injected with the saline or with 2 mg of peptide intravenously. On the indicted day, the animals were sacrificed and a single cell suspension of splenocytes was prepared. Cells were cultured under limiting dilution conditions using irradiated (2000 R) splenocytes from Lewis rats as stimulators. After 5 days, wells were assayed for lysis against $^{51}$CR-labeled Lewis blasts. CTL precursor frequency was determined by linear regression analysis.

To assess whether the peptides could affect alloreactivity in vivo, we tested their effects on the accumulation of cells in the draining lymph nodes following injection of nonself spleen cells into footpads (Moeller et al. 1993, supra; Twist and Barnes. 1973. *Transplantation*, 15:182; Fanslow et al. 1990. *Science* 248:739). PVG or ACI rats (3 per group) were given a single intravenous injection of 2 mg of each of the four peptides or saline. On the day of treatment, or on days 1, 7, or 10 after treatment, the right footpads were injected with 5×106 syngeneic splenocytes while the left footpads were injected with 5×106 allogeneic Lew splenocytes. Seven days after the footpad injections, the draining lymph nodes were removed, a single cell suspension was prepared, and the cell number determined. The ratio of the number of cells recovered from the side injected with allogeneic versus syngeneic cells was approximately 3:1 in animals treated with saline, the A2.75-84 peptide, or the RT1$^a$.75-84 peptide. A similar ratio was observed in lymph nodes obtained from animals treated with the B7.75-84 or B2702.75-84 peptide within 24 hours of footpad injection. However, the ratio fell to 1:1 in animals treated with the B7.75-84 peptide 7 or 10 days prior to footpad challenge. The ratio in animals treated with the B2702.75-84 peptide 7 or 10 days prior to footpad injection was approximately 2:1, indicating that it was somewhat less effective at suppressing the rat in vivo response to alloantigen.

None of these peptides was able to modulate antibody responses to the soluble protein antigen, keyhole limpet hemocyanin (KLH). Administration of peptides prior to, concomitant with, or following immunization with KLH did not alter the titer of anti-KLH antibody that was detected in serum obtained 7 or 14 days later (not shown).

Cardiac allograft survival is induced by intravenous administration of the B7.75-84 peptide plus a short course of CsA.

Figure 8A:
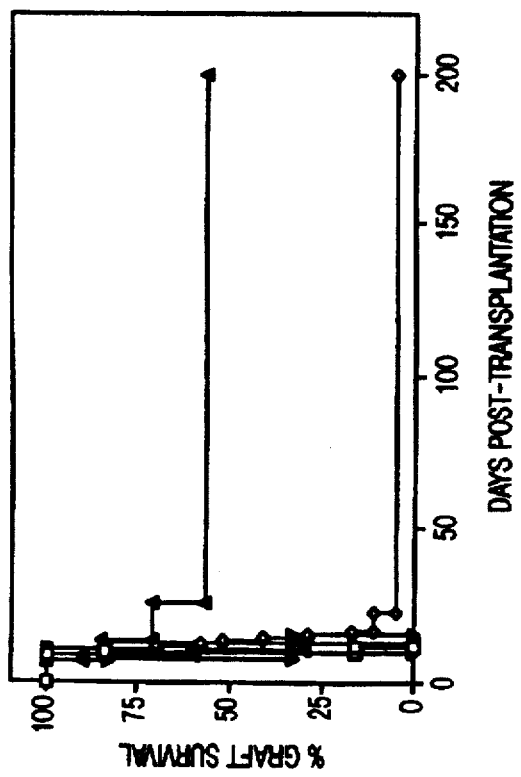
FIG. 8 represents the survival of heterotopic heart allografts. ACI rats were used as recipients for abdominal heterotopic heart allografts from Lew donors. Grafts were palpated daily and were scored as rejected when there was no palpable beat. (A) Animals were treated with B7.75-84 and/or a single dose of CsA on day 2. Animals that received no treatment (n=6) had median graft survival of 10 days. Animals treated with 20 mg of B7.75-84 on days −7 and −1 prior to surgery (n=6), 10 mg of B7.75-84 on days −14, −12, −10 and −7 (n=11), or 20 mg/kg CsA on day 2 (n=17) had a median survival time of 8, 14, and 14 days, respectively. Combination treatment with 20 mg B7.75-84 on days −7 and −1 followed by 20 mg/kg CsA on day 2 after transplantation (n=7) resulted in a median survival time of 13 days. The median graft survival in animals treated with 10 mg of B7.75-84 on days −14, −12, −10 and −7 before surgery and with 20 mg/kg CsA on day 2 (n=7) was 200 days. (B) Animals were treated with B7.75-84 and/or 5 doses of CsA. Animals were treated with 20 mg/kg of B7.75-84 on days −7 and −1 prior to surgery (n=6), 10 mg of B7.75-84 on days 0–4 (n=9), or 10 mg/kg CsA on days 0–4 (n=18), had a median graft survival of 8, 14, 10 and 18 days, respectively. Treatment with the combination of 5 doses of CsA plus 20 mg of B7.75-84 on days −7 and −1 (n=7), or CsA plus 10 mg B7.75-84 on days 0–4 (n=11), or CsA plus 10 mg B7.75-84 on days −14, −12, −10 and −7 (n=29) all had median graft survival of >200 days. (C) Animals were treated with B.2702.75-84 and/or 5 doses of CsA using the same regimen as in (B). Animals treated with 20 mg B2702.75-84 on days −14, −12, −10, and −7 (n=10) or with 10 mg CsA on days 0–4 (n=18) had a median graft survival of 8 and 18 days, respectively. Treatment with a combination of CsA plus 20 mg of B2702.75-84 on days −7 and −1 (n=8), CsA plus 10 mg of B2702.75-84 on days −14, −12, −10 and −7 (n=10), or CsA plus 10 mg of B2702.75-84 on days 0–4 (n=8) had median graft survival of 17, 19 and 13 days, respectively.
Figure 8B:
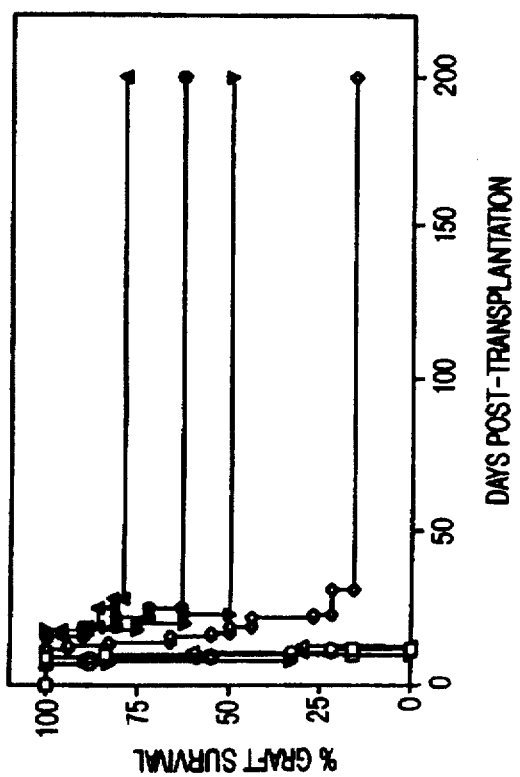

Since the B7.75-84 and B2702.75-84 peptides blocked cellular immunity in vivo, we examined their effects on allograft survival. ACI (RT1$^a$) recipients were given abdominal heterotopic heart allografts from Lew donors (Moeller et al. 1993, supra; Ono and Lindsey. 1969, supra). Graft function was monitored by daily abdominal palpation, and rejection was scored as complete when the palpable ventricular contractions ceased. Grafts survived 9–12 days in control animals receiving no therapy (FIG. 8). Allograft survival was similar (7–13 days) in recipients treated with 2–5 doses of B7.75-84 either in the two weeks before or in the 4 days following the transplant (FIGS. 8a and 8b).

Therefore, we elected to combine peptide therapy with a subtherapeutic regimen of CsA. When CsA was administered as a single dose (20 mg/kg) two days after transplantation, 16 of 17 animals rejected their grafts by day 23 (FIG. 8a). However, 4 of 7 animals that received 4 treatments with 10 mg of B7.75-84 in the two weeks before surgery and a single dose of CsA two days after surgery retained their grafts indefinitely (>200 days) (p=0.0023 compared to CsA alone). All animals treated with 20 mg of B7.75-84 on days −7 and −1 before transplantation and then with a single dose of CsA on day 2 after surgery rejected their grafts by day 16. This result indicates that the timing of peptide administration is critical since the total dose of B7.75-84 given was identical in the two groups.

An alternate treatment protocol in which animals were given CsA (10 mg/kg) daily on days 0–4 after surgery (FIG. 8b) was also evaluated. The majority of these grafts (14/17) were rejected by 30 days after transplantation. Fifty percent (4/8) of animals treated with 20 mg of B7.75-84 on days −7 and −1 prior to transplantation and then given CsA on days 0–4 retained their grafts for >200 days (p=0.0849 compared to CsA alone). This is in contrast to the finding that animals given the identical peptide regimen combined with a single dose of CsA on day 2 (FIG. 8a) rejected their grafts by day 16 (FIG. 8b). Treatment of animals with 10 mg of B7.75-84 on days −14, −12, −10, and −7 followed by CsA on days 0–4 after transplantation resulted in tolerance in 23/29 animals (80%) (p<0.0001 compared to CsA alone). Lastly, 7/11 animals treated concomitantly with B7.75-84 peptide and CsA on days 0–4 after transplantation retained their grafts for >200 days (p=0.0090 compared to CsA alone). In summary, these results indicate that the B7.75-84 peptide could induce graft tolerance when used in combination with a subtherapeutic dose of CsA. Peptide treatment was effective when administered in the period before or after the transplant.

Figure 8C:
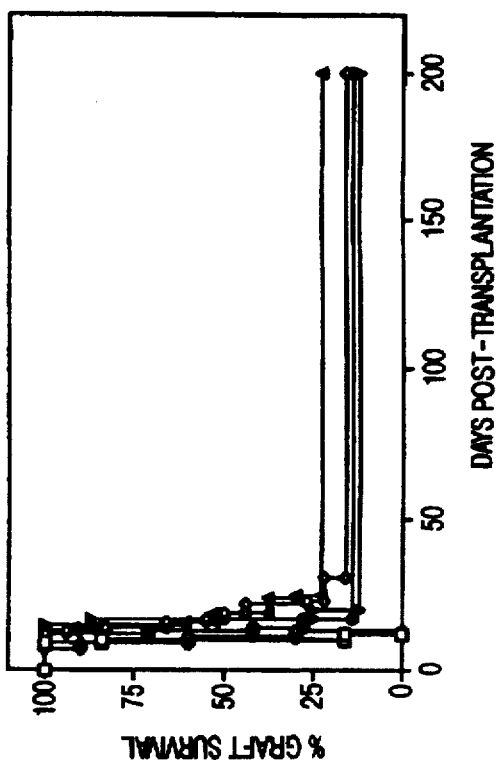

The synergistic effect of CsA and peptide on allograft survival was dependent on the peptide sequence: transplants in animals treated with the B2702.75-84 peptide in the two week period before transplantation or in the 4 days after surgery in combination with CsA on days 0–4 were rejected similarly to allografts in animals treated with CsA alone (FIG. 8c).

Animals treated with the B7.75-84 peptide plus a subtherapeutic dose of CsA exhibit donor specific tolerance.

Although the majority of animals treated with the combination of B7.75-84 plus CsA did not reject their grafts, it remained possible that the animals were not tolerant. Treatment may have produced a general immunosuppressed state or the graft may have lost antigen presenting function or downregulated MHC. To differentiate between tolerance and these other possibilities, animals that had retained their grafts for a minimum of 100 days were retransplanted with a second abdominal heart allograft distal to the primary graft. No further peptide or CsA treatments were given. Animals that received a second heart allograft from Brown Norway (BN) (RT1$^n$) donors (n=4) rejected the BN allograft by day 14 while those that received a second heart graft from the same strain as the original donor (n=3) accepted the second allograft indefinitely. To assess the tissue specificity of this tolerance, animals that had maintained their heart grafts for >100 days were given two full-thickness abdominal skin allografts (n=4): the graft on the left side was from a BN donor and that on the right was from a Lew donor. Again, no additional peptide or CsA was administered. The BN skin grafts were rejected by day 11 while the Lew skin graft showed no signs of rejection (>200 days). Interestingly, rejection of a second allograft (heart or skin) did not affect the function of the original cardiac allograft.

The B7.75-84 peptide administered orally induces specific unresponsiveness.

Figure 9:
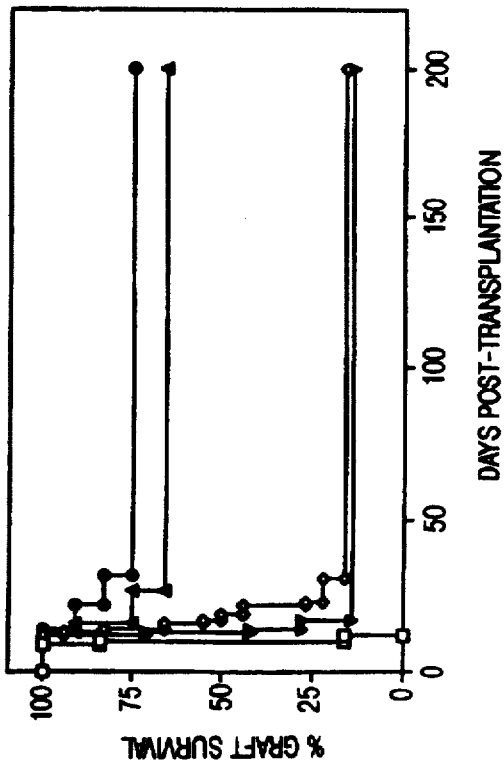
FIG. 9 shows the effect of oral administration of B7.75-84 in preventing allograft rejection. Animals were treated and transplanted as described in relation to FIG. 8 with the exception that the B7.75-84 was given in water by lavage. Animals treated with 10 mg/kg CsA alone on days 0–4 (n=18) had median graft survival of 18 days. Animals treated with the combination of CsA plus 10 g B7.75-84 orally on days 0–4 (n=12) or 10 mg B7.75-84 orally on days −14, −12, −10 and −7 (n=12) had median graft survival of >200 days. Median graft survival in animals treated with CsA plus 10 mg B2702.75-84 orally on days 0–4 (n=9) was 22 days.

The route by which a drug is given can often affect its potency. Carpenter and coworkers have reported that intrathymic injection of synthetic peptides corresponding to non-helical regions of rat MHC class II molecules prolonged the survival of vascularized allografts (Sayegh, et al. 1993. *Transplant Proc.* 25:357). In contrast, Fabre and colleagues found that synthetic peptides corresponding to residues 57–80 of the RT1A$^a$ molecule were immunogenic rather than tolerogenic when administered in complete Freund's adjuvant (Fangmann et al. 1993. *Transplant Proc.* 25:183). We asked whether administration of the B7.75-84 peptide orally would induce tolerance to an allograft. Animals treated with peptide alone rejected their grafts with normal kinetics (FIG. 9). However, 8/12 animals given the peptide orally on days −14, −12, −10, and −7 prior to transplantation and 9/12 animals treated on days 0–4 after surgery in combination with CsA on days 0–4 maintained their grafts for >200 days (FIG. 9) (p=0.005 and 0.0007 respectively, compared with CsA alone). In addition, when the animals that had retained their cardiac allografts were given subsequent skin allografts from donor and third party, they rejected the third party grafts but not the donor skin grafts. Thus, the immunomodulatory effects of the B7.75-84 peptide could be achieved by either oral or intravenous administration.

Anergy is involved in the tolerance induced by the B7.75-84 peptide.

To investigate mechanisms by which the B7.75-84 peptide modified the response to alloantigens, several immunologic parameters were examined. Fluorescence activated cell sorter analysis showed that there were no differences in the absolute number of cells or percentage of CD4+ and CD8+ subsets in thymus or spleen isolated from peptide treated versus naive animals. Mitogen or alloantigen induced proliferation of spleen cells obtained from peptide treated animals was identical to that of controls. In addition, splenocytes from tolerant animals were unable to directly suppress an alloresponse in naive animals, indicating that "suppressor" cells were not involved. However, donor reactive cells could be demonstrated in tolerant animals. Using limiting dilution analysis, we found that the precursor frequency of Lew specific CTL in splenocytes obtained from naive ACI animals was 1 in 303,611. The frequency of Lew specific CTL precursors in splenocytes obtained from ACI rats that had maintained a Lewis heart allograft for more than 100 days was 1 in 98,646. These results suggest that anergic donor reactive cells were present in vivo and that these cells were released from anergy by exogenous cytokines that were added to the limiting dilution cultures in vitro (Jenkins and Miller. 1992. *Faseb J.* 6:2428; Atteis et al. 1991. *J. Exp. Med.* 175:491). It should be noted that the only sequence available for a rat MHC Class I molecule is the RT1A molecule, which is identical where the B7.75-84 in seven of ten amino acids, in contrast to the B2702.75-80 peptide which is identical to the RT1A sequence in only five of ten residues (RT1A.75–84 RVDLRTLRGY (SEQ ID NO:41).

It is evident from the above results that fragments of the polymorphic regions of Class I MHC antigens find use in the modulation of CTL activity for a variety of purposes, particularly to inhibit CTL induced diseases or CTL induced rejection of transplants. Particularly, subject compositions can be used across a broad spectrum of CTLs with different MHC antigens and provide for the protective effect. In addition, the subject compositions may be used to direct molecules to CTLs, where one wishes to concentrate the affect of an agent in relation to the CTLs, as compared to other cells present in the host. Alternatively, the subject compositions may be conjugated to an antigen of interest to activate CTLs to lyse cells carrying antigens other than those recognized by the CTL and thus induce CTL to lyse cells carrying antigens cryptic to the host, as in parasitic diseases in neoplasia. The subject compounds may find use in the treatment of viral diseases. Alternatively, the subject compounds may be used to identify T-cells which specifically bind to one or another of the subject peptides to isolate subsets of CTLs, identify the presence of a particular subset of CTLs, inhibit autoimmune diseases, and the like.

The generic blocking capability of particular peptide compounds allows their general use across a spectrum of hosts and provides an alternate procedure for protecting transplant recipients, without totally debilitating their immune system. Furthermore, the treatment is limited in time, so that the protection continues, long after the immunosuppressant regimen has been terminated. The specific effect of the peptide compounds on the generation of CTLs having particular specificities, allows for sparing memory responses, while blocking the development of donor specific responses.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for blocking CTL activity comprising the step of contacting said CTL with a peptide of 25 amino acids in length or less comprising amino acids 75–84 of a human MHC class I HLA B allele alpha-1 domain protein.

2. The method of claim 1, wherein said peptide has an amino acid sequence comprising amino acids 75–84 of a human MHC class I HLA-B alpha-1 domain protein selected from the group consisting of the human B2702, B38, B7, B62, and Bw46 alleles.

3. The method of claim 2, wherein said peptide has an amino acid sequence comprising amino acids 75–84 of the human HLA-B2702 allele.

4. The method of claim 2, wherein said peptide has an amino acid sequence comprising amino acids 75–84 of the human HLA-B7 allele.

5. A method for blocking CTL activity comprising the step of contacting said CTL with a peptide composition comprising a mutated sequence of amino acids 75–84 of a human MHC class I HLA B allele alpha-1 domain protein, wherein said mutated sequence contains one amino acid substitution from a naturally occurring MHC Class I sequence, and residue 80 is not altered.

6. The method of claim 5, wherein said peptide has an amino acid sequence comprising a mutated sequence of amino acids 75–84 of the human HLA-B2702 allele.

7. The method of claim 5, wherein said peptide has an amino acid sequence comprising a mutated sequence of amino acids 75–84 of the human HLA-B7 allele.

8. A method for blocking CTL activity comprising the step of contacting said CTL with a peptide of 25 amino acids in length or less, wherein said peptide comprises the formula REX$_1$LRIX$_2$X$_3$X$_4$Y (SEQ ID NO:42), wherein X$_1$ is an amino acid selected from the group consisting of D, S, and N, X$_2$ is an amino acid selected from the group consisting of A or L, X$_3$ is an amino acid selected from the group consisting of R and L and X$_4$ is an amino acid selected from the group consisting of G or R.

9. A method for extending the period of acceptance by a recipient host of an allogenic transplant from an MHC unmatched donor host, said method comprising the step of:

administering to said donor host in accordance with a predetermined regimen, in an amount effective to extend the period of acceptance of said allogenic transplant, a combination of (1) an immunosuppressant at a subtherapeutic dosage, and (2) a peptide composition of 25 amino acids in length or less selected from the group consisting of (i) a peptide with an amino acid sequence comprising amino acids 75–84 of a human MHC class I B-type allele alpha-1 domain protein and (ii) a peptide with an amino acid sequence comprising a mutated sequence of amino acids 75–84 of a MHC class I B-type allele alpha-1 domain protein, wherein said mutated sequence contains one amino acid substitution from the naturally occurring sequence and residue 80 is not altered by said mutation;

whereby the period of acceptance of said allogenic transplant is extended as compared to the period which would have resulted from the administering of the immunosuppressant at said subtherapeutic dosage in the absence of said peptide.

10. The method of claim 9, wherein said peptide composition has an amino acid sequence comprising amino acids 75–84 of a human MHC class I HLA-B alpha-1 domain protein selected from the group consisting of the human B2702, B38, B7, B62, and Bw46 alleles.

11. The method of claim 10, wherein said peptide composition has an amino acid sequence comprising amino acids 75–84 of the human HLA-B2702 allele.

12. The method of claim 10, wherein said peptide composition has an amino acid sequence comprising amino acids 75–84 of the human HLA-B7 allele.

13. The method of claim 9, wherein said peptide composition has an amino acid sequence comprising a mutated sequence of amino acids 75–84 of the human HLA-B2702 allele.

14. The method of claim 9, wherein said peptide has an amino acid sequence comprising a mutated sequence of amino acids 75–84 of the human HLA-B7 allele.

15. A method for extending the period of acceptance by a recipient host of an allogenic transplant from an MHC unmatched donor host, said method comprising the step of:

administering to said donor host in accordance with a predetermined regimen, in an amount effective to extend the period of acceptance of said allogenic transplant, a combination of (1) an immunosuppressant at a subtherapeutic dosage, and (2) a peptide of 25 amino acids in length or less wherein said peptide comprises the formula $REX_1LRIX_2X_3X_4Y$, (SEQ ID NO:42) wherein $X_1$ is an amino acid selected from the group consisting of D, S, and N, $X_2$ is an amino acid selected from the group consisting of A or L, $X_3$ is an amino acid selected from the group consisting of R and L and $X_4$ is an amino acid selected from the group consisting of G or R;

whereby the period of acceptance of said allogenic transplant is extended as compared to the period which would have resulted from the administering of the immunosuppressant at said subtherapeutic dosage in the absence of said peptide.

16. An isolated peptide comprising from 2 to 10 copies of a peptide of the amino acid sequence $REX_1LRIX_2LRY$ (SEQ ID NO:43)

wherein $X_1$ and $X_2$ are amino acids selected from the group consisting of C, S, T, M, G, L, I, P, V, N, Q, E, K, and R.

* * * * *

UNITED STATES PATENT AND TRADEMARK OFFICE
CERTIFICATE OF CORRECTION

| | | |
|---|---|---|
| PATENT NO. | : 5,723,128 | Page 1 of 1 |
| APPLICATION NO. | : 08/222851 | |
| DATED | : March 3, 1998 | |
| INVENTOR(S) | : Clayberger et al. | |

It is certified that error appears in the above-identified patent and that said Letters Patent is hereby corrected as shown below:

Column 1: line 15: insert the following:

-- FEDERALLY-SPONSORED RESEARCH OR DEVELOPMENT
This invention was made with Government support under contracts AI041520 and AI022039 awarded by the National Institutes of Health. The Government has certain rights in this invention. --

Signed and Sealed this
Sixth Day of March, 2012

David J. Kappos
*Director of the United States Patent and Trademark Office*